(12) United States Patent
Dietrich et al.

(10) Patent No.: US 8,101,399 B2
(45) Date of Patent: Jan. 24, 2012

(54) ARTEMISINIC EPOXIDE AND METHODS FOR PRODUCING SAME

(75) Inventors: Jeffrey Allen Dietrich, Berkeley, CA (US); Yasuo Yoshikuni, Berkeley, CA (US); Jay D. Keasling, Berkeley, CA (US); Michelle Chia-Yu Chang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 955 days.

(21) Appl. No.: 11/955,154

(22) Filed: Dec. 12, 2007

(65) Prior Publication Data

US 2008/0187983 A1    Aug. 7, 2008

Related U.S. Application Data

(60) Provisional application No. 60/874,600, filed on Dec. 12, 2006.

(51) Int. Cl.
| | |
|---|---|
| *C12N 1/00* | (2006.01) |
| *C12N 1/20* | (2006.01) |
| *C12N 1/21* | (2006.01) |
| *C12N 1/19* | (2006.01) |

(52) U.S. Cl. ............... 435/255.1; 435/252.1; 435/252.3; 435/254.2

(58) Field of Classification Search ................... None
See application file for complete search history.

(56) References Cited

U.S. PATENT DOCUMENTS

| | | |
|---|---|---|
| 2004/0005678 A1 | 1/2004 | Keasling et al. |
| 2005/0059128 A1 | 3/2005 | Arnold et al. |
| 2006/0063226 A1 | 3/2006 | Matuschek et al. |

FOREIGN PATENT DOCUMENTS

WO    WO0031273    6/2000

OTHER PUBLICATIONS

Carmichael et al., "Protein engineering of *Bacillus megaterium* CYP102. The oxidation of polycyclic aromatic hydrocarbons," Eur J. Biochem., 2001, 268(10):3117-3125.

Ravichandran et al., "Crystal structure of hemoprotein domain of P450BM-3, a prototype for microsomal P450's," Science, 1993, 261(5122):731-736.

Ro et al., "Production of the antimalarial drug precursor artemisinic acid in engineered yeast," Nature, 2006, 440 (7086):940-943.

*Primary Examiner* — Michele K Joike
(74) *Attorney, Agent, or Firm* — Paula A. Borden; Bozicevic Field & Francis LLP

(57) ABSTRACT

The present invention provides artemisinic epoxide, and methods of synthesizing artemisinic epoxide in a genetically modified host cell. The present invention further provides methods for producing artemisinin. The present invention further provides variant enzymes that catalyze the oxidation of amorpha-4,11-diene to artemisinic epoxide; nucleic acids encoding the variant enzymes; as well as recombinant vectors and host cells comprising the nucleic acids.

9 Claims, 8 Drawing Sheets

SEQUENCE LISTING

<160> NUMBER OF SEQ ID NOS: 25

<210> SEQ ID NO 1
<211> LENGTH: 1049
<212> TYPE: PRT
<213> ORGANISM: Bacillus megaterium

<400> SEQUENCE: 1

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255
```

```
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
        275                 280                 285
Gln Lys Ala Ala Glu Ala Ala Arg Val Leu Val Asp Pro Val Pro
290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
```

```
                675                 680                 685
Leu Pro Lys Glu Ala Ser Tyr Gln Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
    755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

<210> SEQ ID NO 2
<211> LENGTH: 3150
<212> TYPE: DNA
<213> ORGANISM: Bacillus megaterium

<400> SEQUENCE: 2
atgacaatta aagaaatgcc tcagccaaaa acgtttggag agcttaaaaa tttaccgtta    60

```
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat tggggagac gatgtgaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
```

```
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 3
<211> LENGTH: 1049
<212> TYPE: PRT
<213> ORGANISM: Artificial Sequence
<220> FEATURE:
<223> OTHER INFORMATION: variant cytochrome P450

<400> SEQUENCE: 3

```
Met Ala Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Arg Phe Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240
```

```
Gly Lys Asp Pro Glu Thr Gly Glu Pro Leu Asp Asp Glu Asn Ile Arg
            245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
        275                 280                 285
Gln Lys Ala Ala Glu Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Leu Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
```

Leu Gln Gln Pro Gly Ser Ala Arg Ser Thr Arg His Leu Glu Ile Glu
              675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
        740                 745                 750

Tyr Val Glu Leu Gln Asp Pro Val Thr Arg Thr Gln Leu Arg Ala Met
    755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 4
<211> LENGTH: 3150
<212> TYPE: DNA
<213> ORGANISM: Artificial Sequence
<220> FEATURE:
<223> OTHER INFORMATION: encodes a variant cytochrome P450

```
<400> SEQUENCE: 4
atggcaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tctggtaacg cgcttcttat caagtcagcg tctaattaaa     180
gaagcatgcg atgaatcacg ctttgataaa aacttaagtc aagcgcttaa atttgtacgt     240
gattttgcag gagacgggtt agctacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga cgacctagt agataaaatt     660 attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc caagctacaa acaagtcaaa cagcttaaat atgtcggcat ggtcttaaac     960
gaagcgctgc gcttatggcc aactctgcct gcgttttccc tatatgcaaa agaagatacg    1020
gtgcttggag gagaatatcc tttagaaaaa ggcgacgagc tcatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctggata ttaaagaaac tttaacgtta    1320
aaacctgaag ctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340
```

```
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg ctttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 5
<211> LENGTH: 3150
<212> TYPE: DNA
<213> ORGANISM: Artificial Sequence
<220> FEATURE:
<223> OTHER INFORMATION: codon-optimized sequence encoding cytochrome
      P450

<400> SEQUENCE: 5

```
atggcgatta agaaatgcc tcaacctaaa accttcggtg aactgaaaaa cctgccgctg      60
ctgaacaccg acaagccagt tcaggcactg atgaaaattg ccgacgagct cggcgaaatt     120
ttcaaattcg aagccccagg ccgtgtgacc cgttacctga gcagccagcg tctgattaaa     180
gaggcatgcg acgaatctag atttgataaa aacctgtctc aggccctgaa attcgtgcgt     240
gatttcgcag gtgacggtct gttcacttct tggacccacg aaaagaattg gaaaaaggcc     300
cacaacattc tgctgccttc tttctctcaa caggcaatga aggttatca tgcaatgatg      360 gttgacatcg ctgtccagct ggtccagaaa tgggagcgtc tgaacgcgga tgaacacatt     420
gaagttcctg aagatatgac ccgcctgact ctggacacca ttggcctgtg tggtttcaac     480
taccggttca cagcttcta ccgcgaccag ccgcatccgt tcatcaccag catggtgcgt     540
gctctggacg aagcaatgaa taagctgcag cgcgctaacc cggatgatcc ggcatatgac     600
gaaaacaaac gtcaattcca ggaagatatt aaagtaatga cgatctggt agataagatc      660 atcgcggacc gtaaggctag cggtgagcaa agcgacgacc tgctgacgca catgctgaac     720
ggcaaagacc cggaaacggg tgagccgctg atgacgaaa tatccgtta tcagattatt      780 acctttctga ttgcaggtca cgagactact agcggtctgc tgtccttcgc gctgtacttc     840
ctggtgaaaa atccacatgt gctgcagaag gcggcggaag aagccgcgcg tgtgctggtt     900 gaccccggtgc cgtcctataa acaggtcaaa cagctgaaat atgtaggtat ggttctgaac     960 gaggcctttgc gcctgtggcc gactgctccg gcgttctctc tgtatgcgaa ggaagatact    1020
gttctgggcg gtgaataccc gctcgagaaa ggtgatgaac tgatggtcct gattccgcag    1080
ctgcaccgtg ataagacgat ttgggggcgac gactagaaa aattccgtcc ggagcgtttc    1140
gaaaatcctt ccgctatccc gcagcacgcc ttcaaaccgt ttggtaacgg tcaacgtgct    1200
```

```
tgcattggcc agcaattcgc cctgcacgaa gctacgctgg tgctgggtat gatgctgaag    1260
cacttcgact tcgaggacca tactaactac gagctggaca tcaaagaaac cctgactctg    1320
aagccggagg gtttcgttgt aaagctaaa tccaagaaaa ttccgctggg tggtatccct     1380
tctccttcta cggaacagag cgccaagaaa gttcgtaaaa aggcgaaaaa cgcgcataac    1440
acgccgctgc tggtactgta cggttctaac atgggtactg cggagggcac cgcccgtgat    1500
ctggcggaca tcgcaatgtc caaaggcttc gccccgcaag ttgccaccct ggactcccat    1560
gcgggcaacc tgccgcgtga aggtgccgtt ctgatcgtta ccgcatccta taacggccat    1620
ccgccggata atgcgaaaca gtttgtagac tggctggacc aggcttctgc ggatgaagtg    1680
aaaggtgttc gctatagcgt tttcggttgc ggtgacaaaa actgggcaac tacctaccag    1740
aaagtacctg ccttcatcga cgaaaccctg gccgctaaag gtgctgaaaa cattgcagat    1800
cgtggtgaag ctgatgcgtc cgacgatttt gaaggtacct acgaggaatg cgtgaacac     1860 atgtggtctg atgtggctgc ctatttcaac ctggacatcg aaaactctga agacaacaaa    1920
agcactctgt ccctgcagtt tgttgattct gcggcggata tgccgctggc gaaaatgcac    1980
ggcgcgttca gcaccaatgt ggttgcgtcc aaggaactgc aacagccggg ttctgcacgc    2040
tccacccgcc acctggaaat cgaactgcct aaagaagcga gctaccagga aggtgaccat    2100
ctgggtgtca tcccgcgtaa ctacgaaggt atcgtgaacc gtgtgactgc tcgttttggc    2160
ctggatgcaa gccagcagat tcgcctggaa gccgaagagg aaaaactggc tcatctgccg    2220
ctggctaaaa ctgtaagcgt agaagaactg ctgcagtatg tggaactgca ggacccggtt    2280
actcgcactc aactgcgtgc tatggccgcg aaaaccgtat gtccgccgca caagttgaa     2340 ctggaagcgc tgctggagaa acaggcatac aaagaacagg tactggccaa cgtctgacc    2400 atgctggaac tgctggaaaa atatccggcg tgcgaaatga aattctctga gttcattgcc   2460
ctgctgccgt ccatccgtcc gcgttactac tccatcagct cttcccctcg tgttgacgaa   2520
aaacaggcaa gcattactgt atccgtggtt tccggcgaag cgtggtctgg ttacggcgaa   2580
tataagggca tcgcgagcaa ctacctggct gaactgcaag aaggtgatac catcaccctgc  2640 ttcatttcta ccccgcagtc cgaatttacc ctgccgaaaa cccagagac tccgctgatc   2700 atggtcggtc cgggcaccgg cgttgcaccg ttccgcggtt ttgtacaagc acgtaagcag   2760
ctgaaagagc agggccagtc cctgggtgaa gcgcacctgt acttcggttg tcgttctccg   2820
catgaagact acctgtacca ggaagaactg gagaacgccc agagcgaggg tattattacc   2880
ctgcataccg ctttctctcg tatgccgaac cagccgaaga cctacgtgca gcatgttatg   2940
gaacaggatg gcaagaaact gatcgaactg ctggaccagg cgctcactt ctatatctgc    3000 ggtgatggta gccaaatggc accggcggtc gaagcgacgc tgatgaaaag ctacgcagac   3060
gtgcaccagg ttagcgaggc tgacgcgcgt ctgtggctgc agcagctgga ggagaaaggt   3120
cgttacgcga aagatgtatg ggccggttaa                                   3150
```

<210> SEQ ID NO 6
<211> LENGTH: 1641
<212> TYPE: DNA
<213> ORGANISM: Artificial Sequence
<220> FEATURE:
<223> OTHER INFORMATION: codon-optimized sequence encoding amorphadiene
      synthase

<400> SEQUENCE: 6

```
atggccctga ccgaagagaa accgatccgc ccgatcgcta acttcccgcc gtctatctgg    60
ggtgaccagt tcctgatcta cgaaaagcag gttgagcagg tgttgaaca gatcgtaaac    120
```

```
gacctgaaga aagaagttcg tcagctgctg aaagaagctc tggacatccc gatgaaacac    180
gctaacctgc tgaaactgat cgacgagatc cagcgtctgg gtatcccgta ccacttcgaa    240
cgcgaaatcg accacgcact gcagtgcatc tacgaaacct acggcgacaa ctggaacggc    300
gaccgttctt ctctgtggtt tcgtctgatg cgtaaacagg gctactacgt tacctgtgac    360 gttttaaca actacaagga caagaacggt gctttcaaac agtctctggc taacgacgtt    420
gaaggcctgc tggaactgta cgaagcgacc tccatgcgtg taccgggtga atcatcctg    480 gaggacgcgc tgggttttcac ccgttctcgt ctgtccatta tgactaaaga cgctttctct    540
actaacccgg ctctgttcac cgaaatccag cgtgctctga acagccgct gtggaaacgt    600 ctgccgcgta tcgaagcagc acagtacatt ccgttttacc agcagcagga ctctcacaac    660
aagaccctgc tgaaactggc taagctggaa ttcaacctgc tgcagtctct gcacaaagaa    720
gaactgtctc acgtttgtaa gtggtggaag gcatttgaca tcaagaaaaa cgcgccgtgc    780
ctgcgtgacc gtatcgttga atgttacttc tggggtctgg gttctggtta tgaaccacag    840
tactcccgtg cacgtgtgtt cttcactaaa gctgtagctg ttatcaccct gatcgatgac    900
acttacgatg cttacggcac ctacgaagaa ctgaagatct ttactgaagc gtagaacgc    960 tggtctatca cttgcctgga cactctgccg gagtacatga aaccgatcta caaactgttc    1020
atggatacct acaccgaaat ggaggaattc ctggcaaaag aaggccgtac cgacctgttc    1080
aactgcggta agagtttgt taagaattc gtacgtaacc tgatggttga agctaaatgg    1140
gctaacgaag gccatatccc gactaccgaa gaacatgacc cggttgttat catcaccggc    1200
ggtgcaaacc tgctgaccac cacttgctat ctgggtatgt ccgacatctt taccaaggaa    1260
tctgttgaat gggctgtttc tgcaccgccg ctgttccgtt actccggtat tctgggtcgt    1320
cgtctgaacg acctgatgac ccacaaagca gagcaggaac gtaaacactc ttcctcctct    1380
ctggaatcct acatgaagga atataacgtt aacgaggagt acgcacagac tctgatctat    1440
aaagaagttg aagacgtatg gaaagacatc aaccgtgaat acctgactac taaaaacatc    1500
ccgcgcccgc tgctgatggc agtaatctac ctgtgccagt tcctggaagt acagtacgct    1560
ggtaaagata acttcactcg catgggcgac gaatacaaaac acctgatcaa atccctgctg    1620
gtttacccga tgtccatctg a                                               1641
```

<210> SEQ ID NO 7
<211> LENGTH: 900
<212> TYPE: DNA
<213> ORGANISM: Escherichia coli

<400> SEQUENCE: 7

```
atggactttc gcagcaact cgaagcctgc gttaagcagg ccaaccaggc gctgagccgt     60
tttatcgccc cactgccctt tcagaacact cccgtggtcg aaaccatgca gtatggcgca    120
ttattaggtg gtaagcgcct gcgacctttc ctggtttatg ccaccggtca tatgttcggc    180
gttagcacaa acacgctgga cgcacccgct gccgccgttg agtgtatcca cgcttactca    240
ttaattcatg atgatttacc ggcaatggat gatgacgatc tgcgtcgcgg tttgccaacc    300
tgccatgtga gtttggcga agcaaacgcg attctcgctg gcgacgcttt acaaacgctg    360
gcgttctcga ttttaagcga tgccgatatg ccggaagtgt cggaccgcga cagaattcg    420 atgatttctg aactggcgag cgccagtggt attgccggaa tgtgcggtgg tcaggcatta    480
gatttagacg cggaaggcaa acacgtacct ctggacgcgc ttgagcgtat tcatcgtcat    540
aaaaccggcg cattgattcg cgccgccgtt cgccttggtg cattaagcgc cggagataaa    600
```

| | |
|---|---|
| ggacgtcgtg ctctgccggt actcgacaag tatgcagaga gcatcggcct tgccttccag | 660 |
| gttcaggatg acatcctgga tgtggtggga gatactgcaa cgttgggaaa acgccagggt | 720 |
| gccgaccagc aacttggtaa aagtacctac cctgcacttc tgggtcttga gcaagcccgg | 780 |
| aagaaagccc gggatctgat cgacgatgcc cgtcagtcgc tgaaacaact ggctgaacag | 840 |
| tcactcgata cctcggcact ggaagcgcta gcggactaca tcatccagcg taataaataa | 900 |

<210> SEQ ID NO 8
<211> LENGTH: 549
<212> TYPE: DNA
<213> ORGANISM: Escherichia coli

<400> SEQUENCE: 8

| | |
|---|---|
| atgcaaacgg aacacgtcat tttattgaat gcacagggag ttcccacggg tacgctggaa | 60 |
| aagtatgccg cacacacggc agacacccgc ttacatctcg cgttctccag ttggctgttt | 120 |
| aatgccaaag acaattatt agttacccgc cgcgcactga gcaaaaaagc atggcctggc | 180 |
| gtgtggacta actcggtttg tgggcaccca caactgggag aaagcaacga agacgcagtg | 240 |
| atccgccgtt gccgttatga gcttggcgtg gaaattacgc ctcctgaatc tatctatcct | 300 |
| gactttcgct accgcgccac cgatccgagt ggcattgtgg aaaatgaagt gtgtccggta | 360 |
| tttgccgcac gcaccactag tgcgttacag atcaatgatg atgaagtgat ggattatcaa | 420 |
| tggtgtgatt tagcagatgt attacacggt attgatgcca cgccgtgggc gttcagtccg | 480 |
| tggatggtga tgcaggcgac aaatcgcgaa gccagaaaac gattatctgc atttacccag | 540 |
| cttaaataa | 549 |

<210> SEQ ID NO 9
<211> LENGTH: 16191
<212> TYPE: DNA
<213> ORGANISM: Artificial Sequence
<220> FEATURE:
<223> OTHER INFORMATION: pAM92 plasmid

<400> SEQUENCE: 9

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa agttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg ccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagattcc tggaagatgc caggaagata cttaacaggg aagtgagagg gccgcggcaa | 840 |
| agccgttttt ccataggctc cgcccccctg acaagcatca cgaaatctga cgctcaaatc | 900 |
| agtggtggcg aaacccgaca ggactataaa gataccaggc gtttccccct ggcggctccc | 960 |

```
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aacccccgt tcagtccgac cgctgcgcct tatccggtaa ctatcgtctt      1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt    1320
cgaaaaaccg ccctgcaagg cggttttttc gttttcagag caagagatta cgcgcagacc     1380
aaaacgatct caagaagatc atcttattaa tcagataaaa tatttctaga tttcagtgca    1440
atttatctct tcaaatgtag cacctgaagt cagccccata cgatataagt tgtaattctc     1500
atgtttgaca gcttatcatc gataagcttc cgatggcgcg ccgagaggct ttacacttta     1560
tgcttccggc tcgtataatg tgtggaattg tgagcggata acaattgaat tcaaaggagg     1620
ccatcctggc catgaagaac tgtgtgattg tttctgcggt ccgcacggcg atcggcagct     1680
ttaacggctc tttagcgagc acctctgcaa tcgatctggg tgcgacggtc attaaggccg    1740
ccattgaacg cgccaaaatc gacagccagc acgttgatga ggtgatcatg ggcaatgtgt     1800
tacaagccgg cctgggtcaa aacccagcgc gtcaagcact gttaaaatct ggtctggccg     1860
agaccgtgtg tggcttcacc gtcaataagg tttgcggctc tggcctgaag agcgtggccc     1920 tgcagcacaca agcgattcaa gccggtcagg cacaaagcat cgttgcgggt ggcatggaga     1980
acatgtctct ggcgccgtac ttattagatg ccaaagcccg cagcggttat cgcctgggcg     2040
atggtcaggt gtacgacgtc atcttacgcg atggcttaat gtgcgcgacc cacggttacc     2100
acatgggtat tacggccgaa aacgtggcga agaatacgg cattacgcgc gagatgcagg      2160
atgaattagc actgcactct cagcgcaaag cagcagccgc gatcgagtct ggtgcgttta     2220
cggcggaaat cgtgccagtt aacgtggtca cgcgcaagaa gacgttcgtt ttcagccagg     2280
acgagttccc gaaggcaaac agcaccgcgg aggccttagg tgccttacgc ccagcctttg     2340
acaaagcggg cacggtcacc gccggtaatg cgagcggcat caatgatggt gcagcggcac    2400
tggtcatcat ggaagagagc gccgcattag cagcgggtct gaccccatta gcgcgcatta    2460
aatcttatgc cagcggcggc gtcccaccag ccctgatggg catgggtccg gtcccagcca    2520
cgcaaaaagc cctgcaatta gcgggcctgc aactggccga cattgatctg atcgaggcga    2580
acgaggcgtt tgcagcgcag ttcctggcgg tgggtaagaa tctgggcttc gacagcgaga    2640
aagtcaatgt gaacggtggc gcgattgcgt taggccatcc gattggtgca agcggcgcac    2700
gcatcttagt gacgttactg cacgccatgc aggcacgcga caagacctta ggcctggcga    2760
ccttatgtat tggtggcggt caaggtatcg ccatggtgat cgaacgcctg aactgaagat    2820
ctaggaggaa agcaaaatga aactgagcac caagctgtgc tggtgtggca tcaagggtcg    2880
cctgcgccca caaaagcagc aacagctgca caacacgaac ctgcaaatga ccgagctgaa    2940
aaagcagaag acggccgagc aaaagacccg cccgcagaac gttggcatca agggcatcca    3000
gatttatatc ccgacgcagt gtgtcaacca atctgagctg gagaaattcg atggcgtcag    3060
ccagggtaag tacaccatcg gcctgggcca gaccaacatg agcttcgtga acgaccgtga    3120
ggacatctat tctatgagcc tgacggtgct gtctaagctg atcaagagct acaacatcga    3180
cacgaataag atcggtcgtc tggaggtggg tacggagacg ctgattgaca agagcaaaag    3240
cgtgaagtct gtcttaatgc agctgttcgg cgagaacacg gatgtcgagg gtatcgacac    3300
cctgaacgcg tgttacggcg gcaccaacgc actgttcaat agcctgaact ggattgagag    3360
```

```
caacgcctgg gatggccgcg atgcgatcgt cgtgtgcggc gatatcgcca tctatgacaa   3420
gggtgcggca cgtccgaccg gcggtgcagg caccgttgcg atgtggattg gcccggacgc   3480
accaattgtc ttcgattctg tccgcgcgtc ttacatggag cacgcctacg acttttacaa   3540
gccggacttc acgagcgaat acccgtacgt ggacggccac ttctctctga cctgctatgt   3600
gaaggcgctg gaccaggttt ataagtctta tagcaaaaag gcgatttcta agggcctggt   3660
cagcgacccg gcaggcagcg acgccctgaa cgtgctgaag tatttcgact acaacgtgtt   3720
ccatgtcccg acctgcaaat tagtgaccaa atcttatggc cgcctgttat ataatgattt   3780
ccgtgccaac ccgcagctgt tcccggaggt tgacgccgag ctggcgacgc gtgattacga   3840
cgagagcctg accgacaaga acatcgaaga accttcgtc aacgtcgcga agccgttcca   3900
caaagagcgt gtggcccaaa gcctgatcgt cccgaccaac acgggcaaca tgtataccgc   3960
gtctgtctac gcggcattcg cgagcctgct gaattacgtc ggttctgacg acctgcaggg   4020
caagcgcgtt ggcctgttca gctacggtag cggcttagcg gccagcctgt atagctgcaa   4080
aattgtcggc gacgtccagc acatcatcaa ggagctggac atcaccaaca agctggcgaa   4140
gcgcatcacc gagacgccga aagattacga ggcagcgatc gagttacgcg agaatgcgca   4200
tctgaagaag aacttcaagc cgcaaggtag catcgagcac ctgcagagcg cgtctacta   4260 cctgacgaac attgacgaca gttccgccg ttcttatgac gtcaaaaagt aactagtagg   4320
aggaaaacat catggtgctg acgaacaaaa ccgtcattag cggcagcaag gtgaagtctc   4380
tgagcagcgc ccaaagctct agcagcggcc cgtctagcag cagcgaggag gacgacagcc   4440
gtgacattga gtctctggac aagaagatcc gcccgctgga ggagttagag gccctgctga   4500
gcagcggcaa caccaagcag ctgaagaaca aggaagttgc agcgctggtg atccacggta   4560
agctgccact gtatgcgctg aaaagaaac tgggcgatac gacgcgtgcg gtcgcggtgc   4620
gtcgcaaagc cttaagcatc ttagcggagg ccccggtgtt agccagcgac cgcctgccgt   4680
acaagaacta cgactacgac cgcgtgtttg gcgcgtgctg cgagaatgtc attggctaca   4740
tgccgttacc ggttggtgtg atcggcccgc tggtcattga tggcacgagc tatcacattc   4800
caatggcgac cacggaaggt tgcttagtcg ccagcgccat gcgtggctgt aaggcgatta   4860
acgccggcgg tggcgcgacg accgtgttaa ccaaggatgg tatgacgcgc ggtccggtcg   4920
tccgcttccc aacgctgaag cgcagcggcg cgtgtaagat ttggctggat tctgaggagg   4980
gccaaaacgc gatcaagaaa gccttcaact ctacgagccg tttcgcgcgt ttacagcata   5040
tccagacctg cctggccggc gacctgctgt tcatgcgctt ccgcaccacc acgggcgatg   5100
cgatgggcat gaacatgatc agcaagggcg tcgaatatag cctgaaacaa atggtggaag   5160
aatatggctg ggaggacatg gaggttgtct ctgtgagcgg caactattgc accgacaaga   5220
agccggcagc cattaactgg attgagggtc gcggcaaaag cgtcgtggca gaagcgacca   5280
tcccaggcga cgtggtccgt aaggttctga agagcgacgt cagcgccctg gttgagttaa   5340
atatcgcgaa aaacctggtc ggcagcgcga tggcgggcag cgtgggtggc tttaacgcac   5400
atgcagcgaa tctggttacg gcggtttctt tagccttagg tcaggaccca gcccaaaatg   5460
tcgagagcag caactgcatt accttaatga aagaggttga cggtgacctg cgcatcagcg   5520
tttctatgcc gtctatcgag gtcggcacga tcggcggcgg caccgttta gaaccgcaag   5580 gtgcgatgct ggatctgctg ggcgtgcgcg gcccacatgc aacggcccca ggcaccaatg   5640
cccgccaact ggcccgtatc gtggcctgcg cggttctggc gggtgagctg agcctgtgcg   5700
ccgcattagc cgcgggccat ttagttcaat ctcacatgac ccacaaccgc aagccggcag   5760
```

```
aaccaaccaa gccaaataac ctggacgcaa ccgacattaa ccgtctgaag gatggcagcg    5820
tcacgtgcat taaaagctga gcatgctact aagcttggct gttttggcgg atgagagaag    5880
attttcagcc tgatacagat taaatcagaa cgcagaagcg gtctgataaa acagaatttg    5940
cctggcggca gtagcgcggt ggtcccacct gacccatgc cgaactcaga agtgaaacgc     6000
cgtagcgccg atggtagtgt ggggtctccc catgcgagag tagggaactg ccaggcatca    6060
aataaaacga aaggctcagt cgaaagactg ggcctttcgt tttatctgtt gtttgtcggt    6120
gaacgctctc ctgagtagga caaatccgcc gggagcggat ttgaacgttg cgaagcaacg    6180
gcccggaggg tggcgggcag gacgcccgcc ataaactgcc aggcatcaaa ttaagcagaa    6240
ggccatcctg acggatggcc ttttgcgtt tctacaaact cttttgttta tttttctaaa     6300
tacattcaaa tatgtatccg ctcatgagac aataaccctg cgatcgccga gaggctttac    6360
actttatgct tccggctcgt ataatgtgtg gaattgtgag cggataacaa ttgaattcaa    6420
aggaggctcg agatgtcatt accgttctta acttctgcac cgggaaaggt tattattttt    6480
ggtgaacact ctgctgtgta caacaagcct gccgtcgctg ctagtgtgtc tgcgttgaga    6540
acctacctgc taataagcga gtcatctgca ccagatacta ttgaattgga cttcccggac    6600
attagcttta atcataagtg gtccatcaat gatttcaatg ccatcaccga ggatcaagta    6660
aactcccaaa aattggccaa ggctcaacaa gccaccgatg gcttgtctca ggaactcgtt    6720
agtcttttgg atccgttgtt agctcaacta tccgaatcct tccactacca tgcagcgttt    6780
tgtttcctgt atatgtttgt ttgcctatgc ccccatgcca agaatattaa gttttcttta    6840
aagtctactt tacccatcgg tgctgggttg ggctcaagcg cctctatttc tgtatcactg    6900
gccttagcta tggcctactt ggggggtta ataggatcta atgacttgga aaagctgtca     6960
gaaaacgata agcatatagt gaatcaatgg gccttcatag gtgaaaagtg tattcacggt    7020
accccttcag gaatagataa cgctgtggcc acttatggta atgccctgct atttgaaaaa    7080
gactcacata atggaacaat aaacacaaac aattttaagt tcttagatga tttcccagcc    7140
attccaatga tcctaaccta tactagaatt ccaaggtcta caaaagatct tgttgctcgc    7200
gttcgtgtgt tggtcaccga gaaatttcct gaagttatga agccaattct agatgccatg    7260
ggtgaatgtg ccctacaagg cttagagatc atgactaagt taagtaaatg taaaggcacc    7320
gatgacgagg ctgtagaaac taataatgaa ctgtatgaac aactattgga attgataaga    7380
ataaatcatg gactgcttgt ctcaatcggt gtttctcatc ctggattaga acttattaaa    7440
aatctgagcg atgatttgag aattggctcc acaaaactta ccggtgctgg tggcggcggt    7500
tgctctttga ctttgttacg aagagacatt actcaagagc aaattgacag cttcaaaaag    7560
aaattgcaag atgattttag ttacgagaca tttgaaacag acttgggtgg gactggctgc    7620
tgtttgttaa gcgcaaaaaa tttgaataaa gatcttaaaa tcaaatccct agtattccaa    7680
ttatttgaaa ataaaactac cacaaagcaa caaattgacg atctattatt gccaggaaac    7740
acgaatttac catggacttc ataggaggca gatcaaatgt cagagttgag agccttcagt    7800
gccccaggga aagcgttact agctggtgga tatttagttt tagatacaaa atatgaagca    7860
tttgtagtcg gattatcggc aagaatgcat gctgtagccc atccttacgg ttcattgcaa    7920
gggtctgata agtttgaagt gcgtgtgaaa agtaaacaat ttaaagatgg ggagtggctg    7980
taccatataa gtcctaaaag tggcttcatt cctgtttcga taggcggatc taagaaccct    8040
ttcattgaaa aagttatcgc taacgtattt agctacttta aacctaacat ggacgactac    8100
tgcaatagaa acttgttcgt tattgatatt ttctctgatg atgcctacca ttctcaggag    8160
```

```
gatagcgtta ccgaacatcg tggcaacaga agattgagtt ttcattcgca cagaattgaa    8220
gaagttccca aaacagggct gggctcctcg gcaggtttag tcacagtttt aactacagct    8280
ttggcctcct tttttgtatc ggacctggaa aataatgtag acaaatatag agaagttatt    8340
cataatttag cacaagttgc tcattgtcaa gctcagggta aaattggaag cgggtttgat    8400
gtagcggcgg cagcatatgg atctatcaga tatagaagat tcccacccgc attaatctct    8460
aatttgccag atattggaag tgctacttac ggcagtaaac tggcgcattt ggttgatgaa    8520
gaagactgga atattacgat taaaagtaac catttacctt cgggattaac tttatggatg    8580
ggcgatatta agaatggttc agaaacagta aaactggtcc agaaggtaaa aaattggtat    8640
gattcgcata tgccagaaag cttgaaaata tatacagaac tcgatcatgc aaattctaga    8700
tttatggatg gactatctaa actagatcgc ttacacgaga ctcatgacga ttacagcgat    8760
cagatatttg agtctcttga gaggaatgac tgtacctgtc aaaagtatcc tgaaatcaca    8820
gaagttagag atgcagttgc cacaattaga cgttccttta gaaaaataac taagaatct    8880 ggtgccgata tcgaacctcc cgtacaaact agcttattgg atgattgcca gaccttaaaa    8940
ggagttctta cttgcttaat acctggtgct ggtggttatg acgccattgc agtgattact    9000
aagcaagatg ttgatcttag ggctcaaacc gctaatgaca aagattttc taaggttcaa    9060 tggctggatg taactcaggc tgactggggt gttaggaaag aaaaagatcc ggaaacttat    9120
cttgataaat aggaggtaat actcatgacc gtttacacag catccgttac cgcacccgtc    9180
aacatcgcaa cccttaagta ttgggggaaa agggacacga agttgaatct gcccaccaat    9240
tcgtccatat cagtgacttt atcgcaagat gacctcagaa cgttgacctc tgcggctact    9300
gcacctgagt ttgaacgcga cactttgtgg ttaaatggag aaccacacag catcgacaat    9360
gaaagaactc aaaattgtct gcgcgaccta cgccaattaa gaaaggaaat ggaatcgaag    9420
gacgcctcat tgcccacatt atctcaatgg aaactccaca ttgtctccga aaataacttt    9480
cctacagcag ctggtttagc ttcctccgct gctggctttg ctgcattggt tctctgcaatt    9540 gctaagttat accaattacc acagtcaact tcagaaatat ctagaatagc aagaaagggg    9600
tctggttcag cttgtagatc gttgtttggc ggatacgtgg cctgggaaat gggaaaagct    9660
gaagatggtc atgattccat ggcagtacaa atcgcagaca gctctgactg gcctcagatg    9720
aaagcttgtg tcctagttgt cagcgatatt aaaaaggatg tgagttccac tcagggtatg    9780
caattgaccg tggcaacctc cgaactattt aaagaaagaa ttgaacatgt cgtaccaaag    9840
agatttgaag tcatgcgtaa agccattgtt gaaaaagatt tcgccacctt tgcaaaggaa    9900
acaatgatgg attccaactc tttccatgcc acatgtttgg actctttccc tccaatattc    9960
tacatgaatg acacttccaa gcgtatcatc agttggtgcc acaccattaa tcagttttac   10020
ggagaaacaa tcgttgcata cacgtttgat gcaggtccaa atgctgtgtt gtactactta   10080
gctgaaaatg agtcgaaact cttttgcattt atctataaat tgtttggctc tgttcctgga   10140
tgggacaaga aatttactac tgagcagctt gaggctttca accatcaatt tgaatcatct   10200
aactttactg cacgtgaatt ggatcttgag ttgcaaaagg atgttgccag agtgattta   10260 actcaagtcg gttcaggccc acaagaaaca aacgaatctt tgattgacgc aaagactggt   10320
ctaccaaagg aataactgca gcccgggagg aggattacta tatgcaaacg aaacgtca   10380 ttttattgaa tgcacaggga gttcccacgg gtacgctgga aaagtatgcc gcacacacgg   10440
cagacacccg cttacatctc gcgttctcca gttggctgtt taatgccaaa ggacaattat   10500
tagttacccg ccgcgcactg agcaaaaaag catggcctgg cgtgtggact aactcggttt   10560
```

```
gtgggcaccc acaactggga gaaagcaacg aagacgcagt gatccgccgt tgccgttatg   10620
agcttggcgt ggaaattacg cctcctgaat ctatctatcc tgactttcgc taccgcgcca   10680
ccgatccgag tggcattgtg gaaaatgaag tgtgtccggt atttgccgca cgcaccacta   10740
gtgcgttaca gatcaatgat gatgaagtga tggattatca atggtgtgat ttagcagatg   10800
tattacacgg tattgatgcc acgccgtggg cgttcagtcc gtggatggtg atgcaggcga   10860
caaatcgcga agccagaaaa cgattatctg catttaccca gcttaaataa cccgggggat   10920
ccactagttc tagagcggcc gccaccgcgg aggaggaatg agtaatggac tttccgcagc   10980
aactcgaagc ctgcgttaag caggccaacc aggcgctgag ccgttttatc gccccactgc   11040
cctttcagaa cactcccgtg gtcgaaacca tgcagtatgg cgcattatta ggtggtaagc   11100
gcctgcgacc tttcctggtt tatgccaccg gtcatatgtt cggcgttagc acaaacacgc   11160
tggacgcacc cgctgccgcc gttgagtgta tccacgctta ctcattaatt catgatgatt   11220
taccggcaat ggatgatgac gatctgcgtc gcggtttgcc aacctgccat gtgaagtttg   11280
gcgaagcaaa cgcgattctc gctggcgacg ctttacaaac gctggcgttc tcgattttaa   11340
gcgatgccga tatgccggaa gtgtcggacc gcgacagaat ttcgatgatt tctgaactgg   11400
cgagcgccag tggtattgcc ggaatgtgcg gtggtcaggc attagattta gacgcggaag   11460
gcaaacacgt acctctggac gcgcttgagc gtattcatcg tcataaaacc ggcgcattga   11520
ttcgcgccgc cgttcgcctt ggtgcattaa gcgccggaga taaggacgt cgtgctctgc   11580 cggtactcga caagtatgca gagagcatcg gccttgcctt ccaggttcag gatgacatcc   11640
tggatgtggt gggagatact gcaacgttgg gaaaacgcca gggtgccgac cagcaacttg   11700
gtaaaagtac ctaccctgca cttctgggtc ttgagcaagc ccggaagaaa gcccgggatc   11760
tgatcgacga tgcccgtcag tcgctgaaac aactggctga acagtcactc gatacctcgg   11820
cactggaagc gctagcggac tacatcatcc agcgtaataa ataagagctc caattcgccc   11880
tatagtgaga cgcgtgctag aggcatcaaa taaaacgaaa ggctcagtcg aaagactggg   11940
cctttcgttt tatctgttgt ttgtcggtga acgctctcct gagttaatta atcagatgga   12000
catcgggtaa accagcaggg atttgatcag gtgtttgtat tcgtcgccca tgcgagtgaa   12060
gttatcttta ccagcgtact gtacttccag gaactggcac aggtagatta ctgccatcag   12120
cagcgggcgc gggatgtttt tagtagtcag gtattcacgg ttgatgtctt tccatacgtc   12180
ttcaacttct ttatagatca gagtctgtgc gtactcctcg ttaacgttat attccttcat   12240
gtaggattcc agagaggagg aagagtgttt acgttcctgc tctgctttgt gggtcatcag   12300
gtcgttcaga cgacgaccca gaataccgga gtaacggaac agcggcggtg cagaaacagc   12360
ccattcaaca gattccttgg taaagatgtc ggacataccc agatagcaag tggtggtcag   12420
caggtttgca ccgccggtga tgataacaac cgggtcatgt tcttcggtag tcggatatg    12480 gccttcgtta gcccatttag cttcaaccat caggttacgt acgaattctt taacaaactc   12540
tttaccgcag ttgaacaggt cggtacggcc ttcttttgcc aggaattcct ccatttcggt   12600
gtaggtatcc atgaacagtt tgtagatcgg tttcatgtac tccggcagag tgtccaggca   12660
agtgatagac cagcgttcta cagcttcagt aaagatcttc agttcttcgt aggtgccgta   12720
agcatcgtaa gtgtcatcga tcagggtgat aacagctaca gctttagtga agaacacacg   12780
tgcacgggag tactgtggtt cataaccaga cccagaccc cagaagtaac attcaacgat   12840
acggtcacgc aggcacggcg cgttttctt gatgtcaaat gccttccacc acttacaaac   12900
gtgagacagt tcttctttgt gcagagactg cagcaggttg aattccagct tagccagttt   12960
```

```
cagcagggtc ttgttgtgag agtcctgctg ctggtaaaac ggaatgtact gtgctgcttc    13020
gatacgcggc agacgtttcc acagcggctg tttcagagca cgctggattt cggtgaacag    13080
agccgggtta gtagagaaag cgtctttagt cataatggac agacgagaac gggtgaaacc    13140
cagcgcgtcc tccaggatga tttcacccgg tacacgcatg gaggtcgctt cgtacagttc    13200
cagcaggcct tcaacgtcgt tagccagaga ctgtttgaaa gcaccgttct tgtccttgta    13260
gttgttaaaa acgtcacagg taacgtagta gccctgttta cgcatcagac gaaaccacag    13320
agaagaacgg tcgccgttcc agttgtcgcc gtaggtttcg tagatgcact gcagtgcgtg    13380
gtcgatttcg cgttcgaagt ggtacgggat acccagacgc tggatctcgt cgatcagttt    13440
cagcaggtta gcgtgtttca tcgggatgtc cagagcttct ttcagcagct gacgaacttc    13500
tttcttcagg tcgtttacga tctgttcaac accctgctca acctgctttt cgtagatcag    13560
gaactggtca ccccagatag acggcgggaa gttagcgatc gggcggatcg gtttctcttc    13620
ggtcagggcc atggtctgtt tcctgtgtga aattgttatc cgctcacaat tccacacatt    13680
atacgagccg gatgattaat tgtcaacagc tcatttcaga atatttgcca gaaccgttat    13740
gatgtcggcg caaaaaacat tatccagaac gggagtgcgc cttgagcgac acgaattatg    13800
cagtgattta cgacctgcac agccatacca gcttccga tggctgcctg acgccagaag    13860
cattggtgca ccgtgcagtc gatgataagc tgtcaaacca gatcaattcg cgctaactca    13920
cattaattgc gttgcgctca ctgcccgctt tccagtcggg aaacctgtcg tgccagctgc    13980
attaatgaat cggccaacgc gcggggagag cggtttgcg tattgggcgc cagggtggtt    14040
tttcttttca ccagtgagac gggcaacagc tgattgccct tcaccgcctg gccctgagag    14100
agttgcagca agcggtccac gctggttttgc cccagcaggc gaaaatcctg tttgatggtg    14160
gttgacggcg ggatataaca tgagctgtct tcggtatcgt cgtatcccac taccgagata    14220
tccgcaccaa cgcgcagccc ggactcggta atggcgcgca ttgcgcccag cgccatctga    14280
tcgttggcaa ccagcatcgc agtgggaacg atgccctcat tcagcatttg catggtttgt    14340
tgaaaaccgg acatggcact ccagtcgcct tcccgttccg ctatcggctg aatttgattg    14400
cgagtgagat atttatgcca gccagccaga cgcagacgcg ccgagacaga acttaatggg    14460
cccgctaaca gcgcgatttg ctggtgaccc aatgcgacca gatgctccac gcccagtcgc    14520
gtaccgtctt catgggagaa aataatactg ttgatgggtg tctggtcaga gacatcaaga    14580
aataacgccg gaacattagt gcaggcagct tccacagcaa tggcatcctg gtcatccagc    14640
ggatagttaa tgatcagccc actgacgcgt tgcgcgagaa gattgtgcac cgccgcttta    14700
caggcttcga cgccgcttcg ttctaccatc gacaccacca cgctggcacc cagttgatcg    14760
gcgcgagatt taatcgccgc gacaatttgc gacggcgcgt gcagggccag actggaggtg    14820
gcaacgccaa tcagcaacga ctgtttgccc gccagttgtt gtgccacgcg ttgggaatg    14880 taattcagct ccgccatcgc cgcttccact ttttcccgcg ttttcgcaga aacgtggctg    14940
gcctggttca ccacgcggga aacggtctga taagagacac cggcatactc tgcgacatcg    15000
tataacgtta ctggtttcac attcaccacc ctgaattgac tctcttccgg gcgctatcat    15060
gccataccgc gaaaggtttt gcaccattcg atggtgtcaa cgtaaatgca tgccgcttcg    15120
ccttcgcgcg cgggccggcc tacgcgttta aacttccggt taacgccatg agcggcctca    15180
tttcttattc tgagttacaa cagtccgcac cgctgccggt agctccttcc ggtgggcgcg    15240
gggcatgact atcgtcgccg cacttatgac tgtcttcttt atcatgcaac tcgtaggaca    15300
ggtgccggca gcgcccaaca gtcccccggc cacggggcct gccaccatac ccacgccgaa    15360
```

```
acaagcgccc tgcaccatta tgttccggat ctgcatcgca ggatgctgct ggctaccctg   15420
tggaacacct acatctgtat taacgaagcg ctaaccgttt ttatcaggct ctgggaggca   15480
gaataaatga tcatatcgtc aattattacc tccacgggga gagcctgagc aaactggcct   15540
caggcatttg agaagcacac ggtcacactg cttccggtag tcaataaacc ggtaaaccag   15600
caatagacat aagcggctat ttaacgaccc tgccctgaac cgacgaccgg gtcgaatttg   15660
ctttcgaatt tctgccattc atccgcttat tatcacttat tcaggcgtag caccaggcgt   15720
ttaagggcac caataactgc cttaaaaaaa ttacgccccg ccctgccact catcgcagta   15780
ctgttgtaat tcattaagca ttctgccgac atggaagcca tcacagacgg catgatgaac   15840
ctgaatcgcc agcggcatca gcaccttgtc gccttgcgta taatatttgc ccatggtgaa   15900
aacgggggcg aagaagttgt ccatattggc cacgtttaaa tcaaaactgg tgaaactcac   15960
ccagggattg gctgagacga aaaacatatt ctcaataaac cctttaggga ataggccag    16020 gttttcaccg taacacgcca catcttgcga atatatgtgt agaaactgcc ggaaatcgtc   16080
gtggtattca ctccagagcg atgaaaacgt ttcagtttgc tcatggaaaa cggtgtaaca   16140
agggtgaaca ctatcccata tcaccagctc accgtctttc attgccatac g            16191
```

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
gcgcgttggt gcggatatc                                                  19

<210> SEQ ID NO 11
<211> LENGTH: 37
<212> TYPE: DNA
<213> ORGANISM: Artificial Sequence
<220> FEATURE:
<223> OTHER INFORMATION: primer

<400> SEQUENCE: 11
attgccatgg gcttattctg tttcctgtgt gaaattg                              37

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
catgccatga caattaaaga aatgcc                                          26

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
ttcatgcgtc cagcttgtag ctaacccgtc tcctgcaaa                            39

<210> SEQ ID NO 14
<211> LENGTH: 45

```
<212> TYPE: DNA
<213> ORGANISM: Artificial Sequence
<220> FEATURE:
<223> OTHER INFORMATION: primer

<400> SEQUENCE: 14
acgctgactt gataagaagc gcgttaccag accaggcgcc tcgaa                45

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
agaaccatga gctcgtcgcc tttttctaaa ggatat                          36

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
tttgcaggag acgggttagc tacaagctgg acgcatgaa                       39

<210> SEQ ID NO 17
<211> LENGTH: 45
<212> TYPE: DNA
<213> ORGANISM: Artificial Sequence
<220> FEATURE:
<223> OTHER INFORMATION: primer

<400> SEQUENCE: 17
ttcgaggcgc ctggtctggt aacgcgcttc ttatcaagtc agcgt                45

<210> SEQ ID NO 18
<211> LENGTH: 39
<212> TYPE: DNA
<213> ORGANISM: Artificial Sequence
<220> FEATURE:
<221> NAME/KEY: misc_feature
<222> LOCATION: 21
<223> OTHER INFORMATION: n = a, g, c, or t
<220> FEATURE:
<223> OTHER INFORMATION: primer
<220> FEATURE:
<221> NAME/KEY: misc_feature
<222> LOCATION: (19)...(19)
<223> OTHER INFORMATION: s = g or c
<220> FEATURE:
<221> NAME/KEY: misc_feature
<222> LOCATION: (20)...(20)
<223> OTHER INFORMATION: n = a, g, c, or t

<400> SEQUENCE: 18
ttcatgcgtc cagcttgtsn ntaacccgtc tcctgcaaa                       39

<210> SEQ ID NO 19
<211> LENGTH: 39
<212> TYPE: DNA
<213> ORGANISM: Artificial Sequence
<220> FEATURE:
<221> NAME/KEY: misc_feature
<222> LOCATION: 21
<223> OTHER INFORMATION: n = a, g, c, or t
<220> FEATURE:
<223> OTHER INFORMATION: primer
```

```
<220> FEATURE:
<221> NAME/KEY: misc_feature
<222> LOCATION: (19)...(19)
<223> OTHER INFORMATION: s = g or c
<220> FEATURE:
<221> NAME/KEY: misc_feature
<222> LOCATION: (20)...(20)
<223> OTHER INFORMATION: n = a, g, c, or t

<400> SEQUENCE: 19
tgttgtttcg tgtcccgcsn ntaagaatgt aataatttg                              39

<210> SEQ ID NO 20
<211> LENGTH: 39
<212> TYPE: DNA
<213> ORGANISM: Artificial Sequence
<220> FEATURE:
<221> NAME/KEY: misc_feature
<222> LOCATION: 21
<223> OTHER INFORMATION: n = a, g, c, or t
<220> FEATURE:
<223> OTHER INFORMATION: primer
<220> FEATURE:
<221> NAME/KEY: misc_feature
<222> LOCATION: (19)...(19)
<223> OTHER INFORMATION: s = g or c
<220> FEATURE:
<221> NAME/KEY: misc_feature
<222> LOCATION: (20)...(20)
<223> OTHER INFORMATION: n = a, g, c, or t

<400> SEQUENCE: 20
acttgttgtt tcgtgtccsn naattaagaa tgtaataat                              39

<210> SEQ ID NO 21
<211> LENGTH: 37
<212> TYPE: DNA
<213> ORGANISM: Artificial Sequence
<220> FEATURE:
<221> NAME/KEY: misc_feature
<222> LOCATION: (19)...(19)
<223> OTHER INFORMATION: n = a, c, g, or t
<220> FEATURE:
<223> OTHER INFORMATION: primer
<220> FEATURE:
<221> NAME/KEY: misc_feature
<222> LOCATION: (18)...(18)
<223> OTHER INFORMATION: n = a, g, c, or t
<220> FEATURE:
<221> NAME/KEY: misc_feature
<222> LOCATION: (17)...(17)
<223> OTHER INFORMATION: s = g or c

<400> SEQUENCE: 21
atatagggaa aacaggsnna gttggccata agcgcag                                37

<210> SEQ ID NO 22
<211> LENGTH: 39
<212> TYPE: DNA
<213> ORGANISM: Artificial Sequence
<220> FEATURE:
<221> NAME/KEY: misc_feature
<222> LOCATION: (21)...(21)
<223> OTHER INFORMATION: s = g or c
<220> FEATURE:
<223> OTHER INFORMATION: primer
<220> FEATURE:
<221> NAME/KEY: misc_feature
<222> LOCATION: (20)...(20)
<223> OTHER INFORMATION: n = a, g, c, or t
<220> FEATURE:
<221> NAME/KEY: misc_feature
<222> LOCATION: (19)...(19)
<223> OTHER INFORMATION: n = a, g, c, or t
```

```
<400> SEQUENCE: 22
tttgcaggag acgggttann sacaagctgg acgcatgaa                    39

<210> SEQ ID NO 23
<211> LENGTH: 39
<212> TYPE: DNA
<213> ORGANISM: Artificial Sequence
<220> FEATURE:
<221> NAME/KEY: misc_feature
<222> LOCATION: (21)...(21)
<223> OTHER INFORMATION: s = g or c
<220> FEATURE:
<223> OTHER INFORMATION: primer
<220> FEATURE:
<221> NAME/KEY: misc_feature
<222> LOCATION: (20)...(20)
<223> OTHER INFORMATION: n = a, g, c, or t
<220> FEATURE:
<221> NAME/KEY: misc_feature
<222> LOCATION: (19)...(19)
<223> OTHER INFORMATION: n = a, g, c, or t

<400> SEQUENCE: 23
caaattatta cattcttann sgcgggacac gaaacaaca                    39

<210> SEQ ID NO 24
<211> LENGTH: 39
<212> TYPE: DNA
<213> ORGANISM: Artificial Sequence
<220> FEATURE:
<221> NAME/KEY: misc_feature
<222> LOCATION: (19)...(19)
<223> OTHER INFORMATION: n = a, c, g, or t
<220> FEATURE:
<223> OTHER INFORMATION: primer
<220> FEATURE:
<221> NAME/KEY: misc_feature
<222> LOCATION: (20)...(20)
<223> OTHER INFORMATION: n = a, g, c, or t
<220> FEATURE:
<221> NAME/KEY: misc_feature
<222> LOCATION: (21)...(21)
<223> OTHER INFORMATION: s = g or c

<400> SEQUENCE: 24
attattacat tcttaattnn sggacacgaa acaacaagt                    39

<210> SEQ ID NO 25
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)...(19)
<223> OTHER INFORMATION: n = a, g, c, or t
<220> FEATURE:
<221> NAME/KEY: misc_feature
<222> LOCATION: (20)...(20)
<223> OTHER INFORMATION: n = a, g, c, or t
<220> FEATURE:
<221> NAME/KEY: misc_feature
<222> LOCATION: (21)...(21)
<223> OTHER INFORMATION: s = g or c

<400> SEQUENCE: 25
ctgcgcttat ggccaactnn scctgcgttt tccctatat                    39
```

ARTEMISINIC EPOXIDE AND METHODS FOR PRODUCING SAME

CROSS-REFERENCE

This application claims the benefit of U.S. Provisional Patent Application No. 60/874,600, filed Dec. 12, 2006, which application is incorporated herein by reference in its entirety.

BACKGROUND

Malaria is an infectious disease caused by protozoans of the genus *Plasmodium*, and is transmitted by the bite of infected *Anopheles* mosquitoes. The species *P. falciparum* accounts for the preponderance of global morbidity and mortality, and 41 percent of the world's population live in areas where malaria is endemic. Malaria is a preventable and treatable disease but it is estimated to kill one to three million people each year, primarily young children.

Artemisinin is a potent anti-malarial agent produced naturally in the plant *Artemisia annua*. Malaria has become increasingly resistant to first-line drug therapies, but combination drugs containing artemisinin derivatives show nearly 100 percent effectiveness against the malaria parasite. Production of sufficient quantities of artemisinin from natural sources to meet current global demands suffers from a combination of low yield, difficulty of isolating pure compounds, and resource-intensive cultivation.

There is a need in the art for alternative methods of producing artemisinin.

Literature

Carmichael and Wong (2001) *Eur. J. Biochem.* 268:3117; Ravichandran et al. (1993) *Science* 261:731; U.S. Patent Publication No. 2006/0063226; Ro et al. (2006) *Nature* 440:940.

SUMMARY OF THE INVENTION

The present invention provides artemisinic epoxide, and methods of synthesizing artemisinic epoxide in a genetically modified host cell. The present invention further provides methods for producing artemisinin. The present invention further provides variant enzymes that catalyze the oxidation of amorpha-4,11-diene to artemisinic epoxide; nucleic acids encoding the variant enzymes; as well as recombinant vectors and host cells comprising the nucleic acids.

FEATURES OF THE INVENTION

The present invention features a compound of Structure 1:

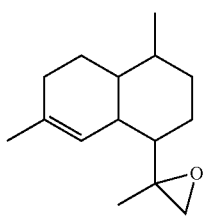

(Structure 1)

In some embodiments, the compound of Structure 1 is substantially pure. In some embodiments, the compound is at least about 80% pure. In some embodiments, the compound is a single stereoisomer. The present invention also features a composition comprising a compound of Structure 1.

The present invention also features a compound of Structure 2:

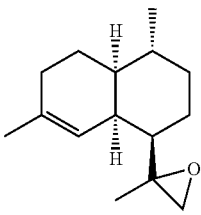

(Structure 2)

In some embodiments, the compound of Structure 2 is substantially pure. In some embodiments, the compound is at least about 80% pure. The present invention also features a composition comprising a compound of Structure 2.

The present invention features a method for synthesizing artemisinic epoxide in a genetically modified host cell. The method generally involves culturing a genetically modified host cell in vitro in a suitable medium, where the genetically modified host cell is one that does not normally synthesize artemisinic epoxide, where the genetically modified host cell is genetically modified with one or more nucleic acids that are heterologous to the host cell and that comprise nucleotide sequences encoding: a) an amorpha-4,11-diene synthase; and b) an enzyme that oxidizes amorpha-4,11-diene to artemisinic-11,12-epoxide, where production of the enzymes in the host cell results in production of artemisinic-11,12-epoxide. In some embodiments, the artemisinic epoxide is produced in a recoverable amount of greater than 400 mg/L. In some embodiments, the artemisinic epoxide is produced in a recoverable amount of from about 400 mg/L to about 500 mg/L. In some embodiments, the artemisinic epoxide is produced in a recoverable amount of from about 500 mg/L to about 1 g/L. In some embodiments, the artemisinic epoxide is produced in a recoverable amount of from about 1 g/L to about 1.5 g/L. In some embodiments, the artemisinic epoxide is produced in a recoverable amount of greater than 1.5 g/L.

In some embodiments of a subject method for synthesizing artemisinic epoxide in a genetically modified host cell, the enzyme that oxidizes amorpha-4,11-diene to artemisinic-11, 12-epoxide is a cytochrome P450 enzyme. In some embodiments, the cytochrome P450 enzyme lacks a transmembrane domain and is soluble in the cytosol of the host cell. In some embodiments, the enzyme that oxidizes amorpha-4,11-diene to artemisinic-11,12-epoxide comprises an R47L substitution, a Y51F substitution, an F87A substitution, and an A328L substitution relative to the amino acid sequence set forth in SEQ ID NO:1. In some embodiments, the nucleotide sequence encoding the enzyme that oxidizes amorpha-4,11-diene to artemisinic-11,12-epoxide is codon-optimized for expression in the genetically modified host cell.

In some embodiments of a subject method for synthesizing artemisinic epoxide in a genetically modified host cell, the method further involves chemically modifying the artemisinic epoxide to generate artemisinin.

In some embodiments of a subject method for synthesizing artemisinic epoxide in a genetically modified host cell, the genetically modified host cell is a eukaryote. For example, in some embodiments, the genetically modified host cell is a yeast cell. In some embodiments, the yeast cell is *Saccharomyces cerevisiae*. In other embodiments, the host cell is a prokaryote.

In some embodiments of a subject method for synthesizing artemisinic epoxide in a genetically modified host cell, the one or more heterologous nucleic acids is integrated into the chromosome of the host cell. In other embodiments, the one or more heterologous nucleic acids is present in a single expression vector. In other embodiments, the one or more heterologous nucleic acids is contained in two or more expression vectors.

In some embodiments of a subject method for synthesizing artemisinic epoxide in a genetically modified host cell, the genetically modified host cell is a prokaryote. For example, in some embodiments, the prokaryote does not normally synthesize isopentenyl pyrophosphate (IPP) via a mevalonate pathway, and the one or more heterologous nucleic acids further comprises nucleotide sequences encoding: (a) one or more mevalonate pathway enzymes, wherein said one or more mevalonate pathway enzymes comprises: i) an enzyme that condenses two molecules of acetyl-CoA to acetoacetyl-CoA; (i) an enzyme that condenses acetoacetyl-CoA with acetyl-CoA to form HMG-CoA; (ii) an enzyme that converts HMG-CoA to mevalonate; (iii) an enzyme that phosphorylates mevalonate to mevalonate 5-phosphate; (iv) an enzyme that converts mevalonate 5-phosphate to mevalonate 5-pyrophosphate; and (v) an enzyme that converts mevalonate 5-pyrophosphate to isopentenyl pyrophosphate; and (b) a farnesyl pyrophosphate synthase. In some embodiments, the one or more heterologous nucleic acids further comprises a nucleic acid comprising a nucleotide sequence coding for an enzyme that converts isopentenyl pyrophosphate to dimethylallyl pyrophosphate. In some embodiments, the one or more heterologous nucleic acids is integrated into the chromosome of the host cell. In some embodiments, the one or more heterologous nucleic acids is contained in two or more operons. In some embodiments, the one or more heterologous nucleic acids is present in a single expression vector. In some embodiments, the one or more heterologous nucleic acids is contained in two or more expression vectors. In some embodiments, the prokaryote is *Escherichia coli*. In some embodiments, the genetically modified host cell has a functionally disabled DXP pathway. In some embodiments, the genetically modified host cell comprises a functionally disabled tryptophanase A gene.

The present invention further features a variant enzyme that oxidizes amorpha-4,11-diene to artemisinic-11,12-epoxide, wherein said variant enzyme comprises an amino acid sequence having at least about 80% amino acid sequence identity to the amino acid sequence set forth in SEQ ID NO:3, wherein said variant enzyme comprises Leu-47, Phe-51, Ala-87 and Leu-328, with the proviso that the enzyme does not comprise the amino acid sequence set forth in SEQ ID NO:1.

The present invention further features a nucleic acid comprising a nucleotide sequence encoding a subject variant enzyme. In some embodiments, the variant enzyme-encoding nucleotide sequence is operably linked to a control element. The present invention further features a recombinant expression vector comprising a subject nucleic acid. The present invention further features a genetically modified host cell comprising a subject nucleic acid, or a subject recombinant vector. In some embodiments, a subject genetically modified host cell is a eukaryotic cell that does not normally produce amorphadiene. In some embodiments, a subject genetically modified host cell is a yeast cell. In some embodiments, a subject genetically modified host cell further comprises a nucleic acid comprising a nucleotide sequence encoding amorphadiene synthase. In some embodiments, a subject genetically modified host cell is a prokaryotic cell. In some embodiments, the prokaryotic host cell does not normally synthesize IPP via a mevalonate pathway, and the genetically modified host cell further comprises one or more heterologous nucleic acids comprising nucleotide sequences encoding one or more mevalonate pathway enzymes. In some embodiments, the genetically modified prokaryotic host cell further comprises a nucleic acid comprising a nucleotide sequence encoding a farnesyl pyrophosphate synthase. In some embodiments, the genetically modified prokaryotic host cell further comprises a nucleic acid comprising a nucleotide sequence encoding amorphadiene synthase. In some embodiments, the genetically modified prokaryotic host cell further comprises a nucleotide sequence encoding an enzyme that converts isopentenyl pyrophosphate to dimethylallyl pyrophosphate.

The present invention features a genetically modified host cell capable of producing amorpha-4,11-diene, where the genetically modified host cell comprises a heterologous cytochrome P450 enzyme that converts amorpha-4,11-diene into amorpha-4-ene-11,12-epoxide. In some embodiments, the amorpha-4,11-diene is produced via a 1-deoxy-D-xylulose 5-diphosphate (DXP) pathway. In some embodiments, the host cell comprises a heterologous nucleotide sequence encoding one or more enzymes of the DXP pathway. In other embodiments, the amorpha-4,11-diene is produced via a mevalonate pathway. In some embodiments, the host cell comprises a heterologous nucleotide sequence encoding one or more enzymes of the mevalonate pathway. In some embodiments, the host cell is a eukaryotic cell, e.g., a yeast cell (e.g., *Saccharomyces cerevisiae*). In other embodiments, the host cell is a prokaryotic cell. In some embodiments, the host cell is *Escherichia coli*.

The present invention features a genetically modified host cell that produces isopentenyl pyrophosphate via a mevalonate pathway, where the genetically modified host cell comprises: a) a heterologous nucleic acid comprising a nucleotide sequence encoding amorphadiene synthase; and b) a heterologous nucleic acid comprising a nucleotide sequence encoding a cytochrome P450 enzyme that converts amorpha-4,11-diene into amorpha-4-ene-11,12-epoxide, wherein said cytochrome P450 enzyme is soluble in the cytosol of said genetically modified host cell. In some embodiments, the genetically modified host cell further comprises a heterologous nucleic acid comprising nucleotide sequences encoding one or more mevalonate pathway enzymes. In some embodiments, the cytochrome P450 enzyme is a variant cytochrome P450 enzyme, e.g., the cytochrome P450 enzyme has an amino acid sequence that differs from the amino acid sequence set forth in SEQ ID NO:1. For example, in some embodiments, the cytochrome P450 comprises a phenylalanine to alanine substitution at amino acid position 87, compared to the amino acid sequence set forth in SEQ ID NO:1; an arginine to leucine substitution at amino acid position 47, compared to the amino acid sequence set forth in SEQ ID NO:1; or a tyrosine to phenylalanine substitution at amino acid position 51, compared to the amino acid sequence set forth in SEQ ID NO:1. In some embodiments, the cytochrome P450 comprises a phenylalanine to alanine at amino acid 87, an arginine to leucine substitution at amino acid 47, and a tyrosine to phenylalanine substitution at amino acid 51, compared to the amino acid sequence set forth in SEQ ID NO:1. In some embodiments, the cytochrome P450 comprises an alanine to leucine substitution at amino acid 328; or an alanine to asparagine substitution at amino acid 328. In some embodiments, the genetically modified host cell comprises a functionally disabled tryptophanase A gene. In some embodiments, the cytochrome P450 comprises the amino acid sequence of SEQ ID NO:1 with an arginine to leucine substitution at amino acid position 47. In other embodiments, the cytochrome P450 comprises the amino acid sequence of SEQ ID NO:1 with a tyrosine to phenylalanine substitution at amino acid position 51. In other embodiments, the cytochrome P450 comprises the amino acid sequence of SEQ ID NO:1 with a phenylalanine to alanine at amino acid 87, an arginine to leucine substitution at amino acid 47, and a tyrosine to phenylalanine substitution at amino acid 51.

The present invention features a genetically modified *Escherichia coli* host cell capable of producing amorpha-4,11-diene via a heterologous mevalonate pathway (e.g., where the genetically modified *Escherichia coli* host cell is genetically modified with one or more nucleic acids comprising nucleotide sequence encoding one or more mevalonate pathway enzymes), where the genetically modified *Escherichia coli* host cell comprises: a) a functionally disabled tryptophanase A gene; and b) a heterologous nucleic acid comprising a nucleotide sequence encoding a variant cytochrome P450 enzyme (e.g., a cytochrome P450 enzyme having an amino acid sequence that differs by at least one amino acid compared to the amino acid sequence set forth in SEQ ID NO:1). For example, in some embodiments, the cytochrome P450 comprises a phenylalanine to alanine substitution at amino acid position 87, compared to the amino acid sequence set forth in SEQ ID NO:1; an arginine to leucine substitution at amino acid position 47, compared to the amino acid sequence set forth in SEQ ID NO:1; or a tyrosine to phenylalanine substitution at amino acid position 51, compared to the amino acid sequence set forth in SEQ ID NO:1. In some embodiments, the cytochrome P450 comprises a phenylalanine to alanine at amino acid 87, an arginine to leucine substitution at amino acid 47, and a tyrosine to phenylalanine substitution at amino acid 51, compared to the amino acid sequence set forth in SEQ ID NO:1. In some embodiments, the cytochrome P450 comprises an alanine to leucine substitution at amino acid 328; or an alanine to asparagine substitution at amino acid 328. In some embodiments, the cytochrome P450 enzyme-encoding nucleotide sequence is codon optimized for expression in *E. coli*.

DEFINITIONS

As used herein, a composition that is a "substantially pure" compound is substantially free of one or more other compounds, i.e., the composition contains greater than 80%, 90%, 95%, 96%, 97%, 98%, 99%, 99.5%, 99.6%, 99.7%, 99.8%, 99.9% by weight of the compound.

Figure 2:
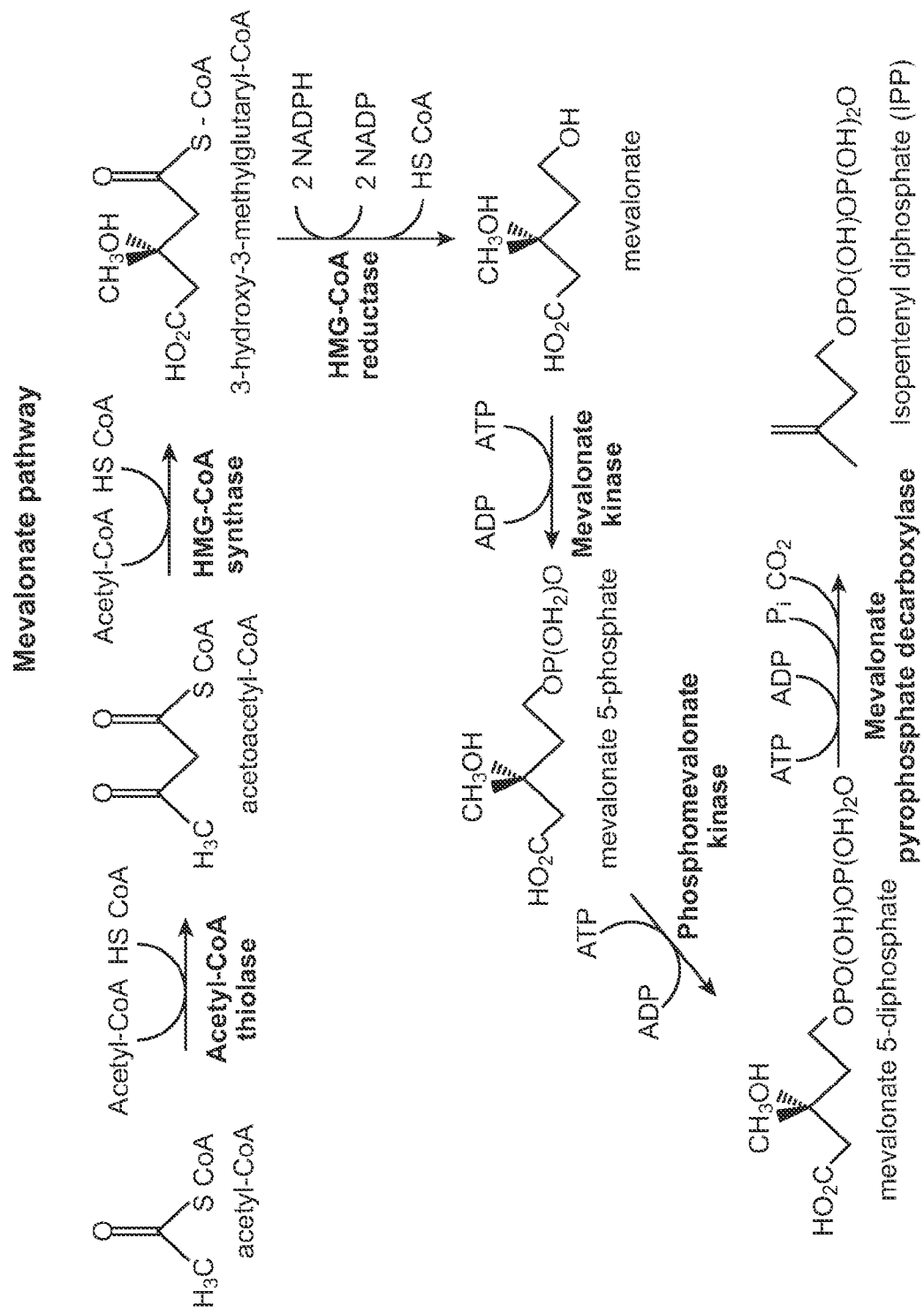
FIG. 2 is a schematic representation of the mevalonate ("MEV") pathway for the production of isopentenyl pyrophosphate ("IPP").

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The mevalonate pathway is illustrated schematically in FIG. 2. The "top half" of the mevalonate pathway refers to the enzymes responsible for the conversion of acetyl-CoA to mevalonate.

Figure 3:
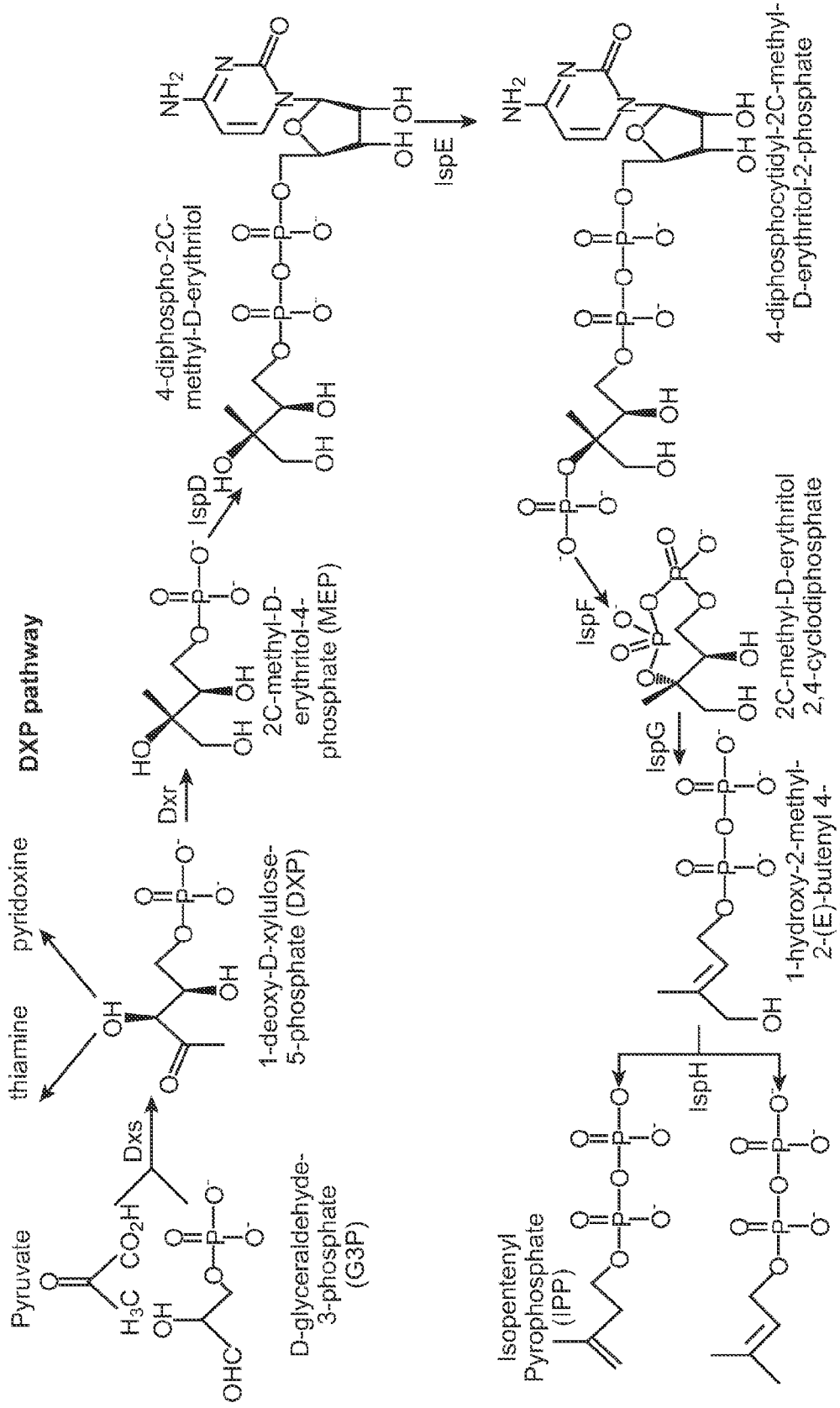
FIG. 3 is a schematic representation of the 1-deoxy-D-xylulose 5-diphosphate ("DXP") pathway for the production of isopentenyl pyrophosphate ("IPP") and dimethylallyl pyrophosphate ("DMAPP").

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 3. Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

The term "heterologous polypeptide," as used herein, refers to a polypeptide that is not naturally associated with a given polypeptide. For example, an isoprenoid precursor-modifying enzyme that comprises a "heterologous transmembrane domain" refers to an isoprenoid precursor-modifying enzyme that comprises a transmembrane domain that is not normally associated with (e.g., not normally contiguous with; not normally found in the same polypeptide chain with) the isoprenoid precursor-modifying enzyme in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject genetically modified prokaryotic host cell (e.g., a bacterium) is a prokaryotic host cell that, by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject genetically modified eukaryotic host cell is a eukaryotic host cell that, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an enzyme that oxidizes amorpha-4,11-diene to artemisinic-11,12-epoxide" includes a plurality of such enzymes and reference to "the recombinant expression vector" includes reference to one or more recombinant expression vectors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides artemisinic epoxide; and methods of synthesizing artemisinic epoxide in a genetically modified host cell. The present invention further provides methods for producing artemisinin. The present invention further provides variant enzymes that catalyze the oxidation of amorpha-4,11-diene to artemisinic epoxide; nucleic acids encoding the variant enzymes; as well as recombinant vectors and host cells comprising the nucleic acids.

Artemisinic Epoxide

Figure 1:
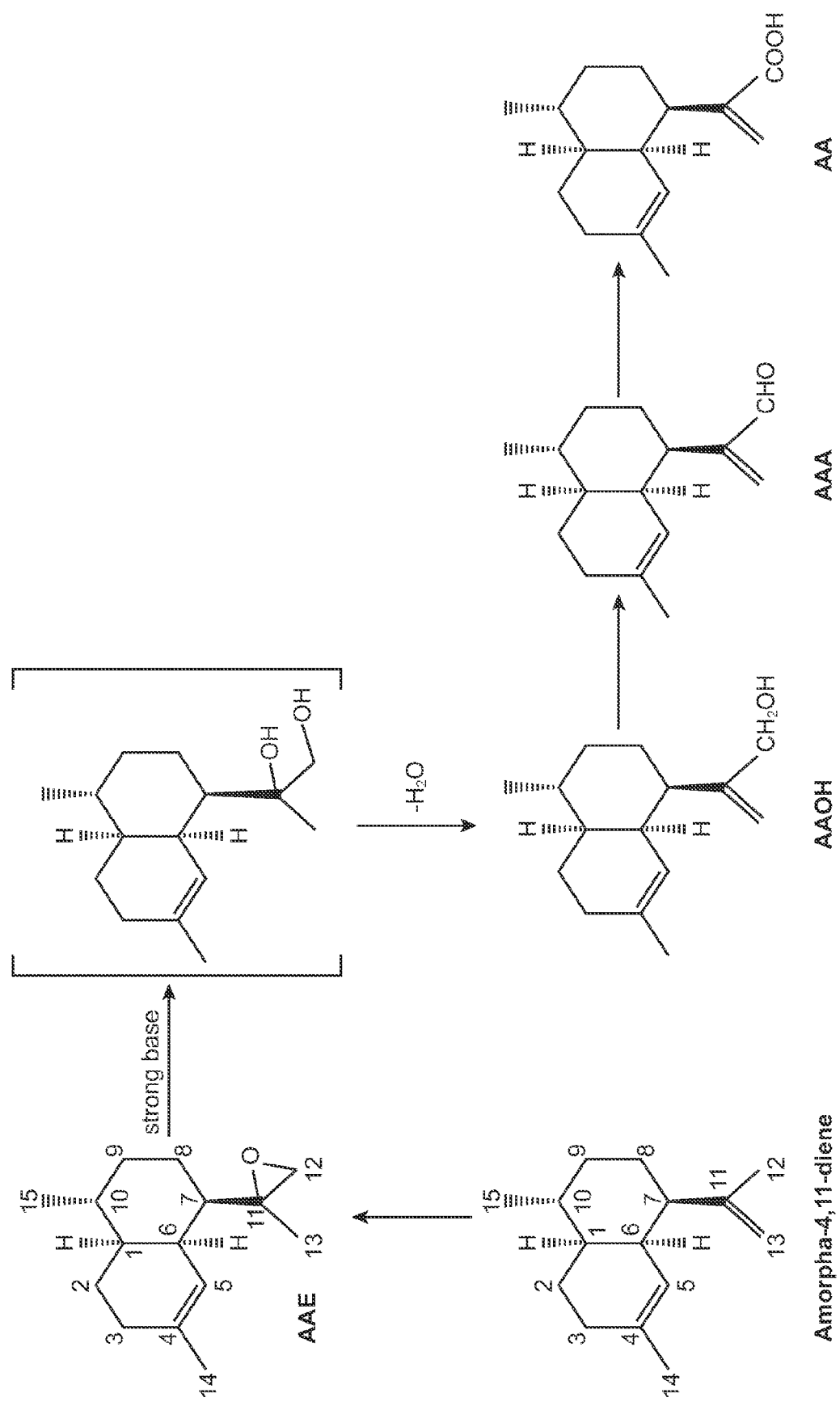
FIG. 1 is a schematic depiction of the conversion of amorpha-4,11-diene to artemisinic acid (AA) via artemisinic-11S,12-epoxide (AAE). (AAOH=artemisinic alcohol; AAA=artemisinic aldehyde).

The present invention provides artemisinic-11,12-epoxide (also referred to herein as "artemisinic epoxide"), as well as compositions comprising artemisinic epoxide. The artemisinic epoxide finds use as an intermediate in the synthesis of artemisinin. As depicted in FIG. 1, amorphadiene can be converted to artemisinic acid through a series of oxidation reactions via the action of a P450 enzyme, CYP71AV1 derived from *Artemisia annua*, where the amorphadiene is oxidized to artemisinic alcohol, followed by a further oxidation step to form artemisinic aldehyde, and finally generating artemisinic acid. Artemisinic acid can then be further modified to generate artemisinin. Ro et al. ((2006) *Nature* 440:940-943. Artemisinic epoxide is an alternative intermediate in the synthesis of artemisinic acid. As depicted in FIG. 1, amorphadiene can be converted to artemisinic epoxide, which can then be converted to artemisinic alcohol, and onward to artemisinic acid.

In some embodiments, the artemisinic epoxide is present in an in vitro cultured cell, e.g., in a cell grown in in vitro culture. In some embodiments, the cell is an isolated cell. In some embodiments, the cell is cultured as a unicellular entity. In some embodiments, the cell is one that does not normally produce artemisinic epoxide, where the cell has been genetically modified to produce artemisinic epoxide, as described in detail below. In some embodiments, the cell is one that does not normally synthesize artemisinic acid or artemisinin. In some embodiments, the cell is a prokaryote that does not normally synthesize artemisinic epoxide, artemisinic acid, or artemisinin, where the prokaryotic cell has been genetically modified to produce artemisinic epoxide, as described in detail below. Suitable prokaryotic cells are described below. In other embodiments, the cell is a eukaryote that does not normally synthesize artemisinic epoxide, artemisinic acid, or artemisinin, where the eukaryotic cell has been genetically modified to produce artemisinic epoxide, as described in detail below. Suitable eukaryotic cells are described below. In some embodiments, the eukaryotic cell is a yeast cell.

In some embodiments, the artemisinic epoxide is present in a cell lysate of a cell that has been genetically modified to produce artemisinic epoxide. In some embodiments, the artemisinic epoxide is present in a fraction of a cell lysate of a cell that has been genetically modified to produce artemisinic epoxide. In other embodiments, the artemisinic epoxide is present in the cell culture medium in which a cell that has been genetically modified to produce artemisinic epoxide is being cultured. In other embodiments, the artemisinic epoxide is present in both a cell that has been genetically modified to produce artemisinic epoxide and the cell culture medium in which the genetically modified cell is being cultured.

Artemisinic epoxide has the following structure:

Structure 1

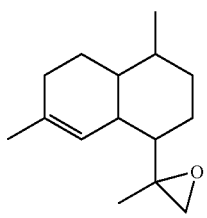

The present invention provides a compound of Structure 1.

In some embodiments, the artemisinic epoxide is substantially pure, e.g., a composition comprising artemisinic epoxide contains greater than 80%, 90%, 95%, 96%, 97%, 98%, 99%, 99.5%, 99.6%, 99.7%, 99.8%, 99.9% by weight of the artemisinic epoxide.

In addition to the definitions above, certain artemisinic epoxide compounds described herein have one or more double bonds that can exist as either the Z or E isomer. The present invention encompasses these compounds as individual isomers substantially free of other isomers and alternatively, as mixtures of various isomers, e.g., racemic mixtures of steroisomers. For example, in some embodiments, a subject artemisinic epoxide compound has the following structure.

Structure 2

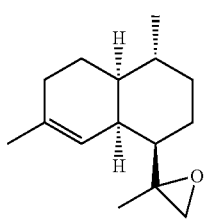

In some embodiments, the artemisinic epoxide isomer is substantially pure, e.g., a composition comprising an artemisinic epoxide isomer contains greater than 80%, 90%, 95%, 96%, 97%, 98%, 99%, 99.5%, 99.6%, 99.7%, 99.8%, 99.9% by weight of the artemisinic epoxide isomer. In some embodiments, a subject composition comprises substantially pure E isomer of artemisinic epoxide. In other embodiments, a subject composition comprises substantially pure Z isomer of artemisinic epoxide.

Methods of Producing Artemisinic Epoxide

The present invention provides methods of synthesizing artemisinic epoxide in a genetically modified host cell. The methods generally involve culturing a genetically modified host cell in a suitable medium, where the genetically modified host cell is one that does not normally synthesize artemisinic epoxide, and where the genetically modified host cell is one that has been genetically modified with one or more nucleic acids heterologous to the host cell, where the one or more nucleic acids comprises nucleotide sequences encoding: a) an amorph-4,11-diene synthase; and b) an enzyme that oxidizes amorpha-4,11-diene to artemisinic-11,12-epoxide. The encoded enzymes are synthesized by the genetically modified host cell. Production of the enzymes results in production of artemisinic-11,12-epoxide by the genetically modified host cell.

In some embodiments, the amount of artemisinic epoxide produced by the genetically modified host cell, e.g., by a culture of the genetically modified host cell, is greater than 400 mg/L. For example, in some embodiments, the amount of artemisinic epoxide produced by a genetically modified host cell, e.g., by a culture of a genetically modified host cell, is from about 400 mg/L to about 450 mg/L, from about 450 mg/L to about 500 mg/L, from about 500 mg/L to about 750 mg/L, from about 750 mg/L to about 1000 mg/L, from about 1000 mg/L to about 1250 mg/L, from about 1250 mg/L to about 1500 mg/L, from about 1500 mg/L to about 2000 mg/L, from about 2000 mg/L to about 3000 mg/L, from about 3000 mg/L to about 4000 mg/L, or from about 4000 mg/L to about 5000 mg/L. Production levels are expressed on a per unit volume (e.g., per liter) cell culture basis.

The produced artemisinic epoxide can be recovered from the medium or from the host cell (e.g., from the culture medium in which the genetically modified host cell is grown) and/or from a cell lysate or a fraction of a cell lysate. The level of artemisinic epoxide produced is readily determined using well-known methods, e.g., gas chromatography-mass spectrometry, liquid chromatography-mass spectrometry, ion chromatography-mass spectrometry, thin layer chromatography, pulsed amperometric detection, uv-vis spectrometry, and the like. In some embodiments, the artemisinic epoxide is recovered from the cell culture medium in which the genetically modified host cells are cultured and/or is recovered from the genetically modified host cells; and the recovered artemisinic epoxide is further modified chemically (e.g., in a cell-free reaction) to generate one or more downstream product(s) such as artemisinic-11,12-diol, artemisinic alcohol, artemisinic aldehyde, artemisinic acid, and artemisinin.

Genetically Modified Host Cells; Parent Host Cells

The genetically modified host cell is generated by genetically modifying a parent host cell. The parent cell is one that does not normally produce artemisinic epoxide or artemisinin. In some embodiments, the parent host cell is a eukaryotic host cell that does not normally produce artemisinic epoxide or artemisinin. In other embodiments, the parent cell is a prokaryotic host cell that does not normally produce artemisinic epoxide or artemisinin. In some embodiments, the parent cell is a prokaryotic host cell that does not normally synthesize isopentenyl pyrophosphate (IPP) via a mevalonate pathway.

In some embodiments, genetically modified host cells are unicellular organisms, or are grown in culture as single cells. In some embodiments, a genetically modified host cell is an in vitro host cell. In other embodiments, a genetically modified host cell is an in vivo host cell.

Eukaryotic Host Cells

In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum,*

*Fusarium venenatum, Neurospora crassa, Chlamydomonas reinhardtii*, and the like. In some embodiments, the host cell is a eukaryotic cell other than a plant cell.

In other embodiments, the host cell is a plant cell. Plant cells include cells of monocotyledons ("monocots") and dicotyledons ("dicots").

Where the genetically modified host cell is a genetically modified version of a parent eukaryotic cell that does not normally synthesize artemisinic epoxide or artemisinin, in some embodiments, the one or more heterologous nucleic acids further comprises a nucleotide sequence encoding a farnesyl pyrophosphate synthase, e.g., an FPP synthase that is heterologous to the host cell. In some embodiments, the one or more heterologous nucleic acids further comprises a nucleotide sequence encoding an IPP isomerase, e.g., an IPP isomerase that is heterologous to the host cell. In some embodiments, the one or more heterologous nucleic acids further comprises a nucleotide sequence encoding one or more DXP pathway enzymes.

Prokaryotic Host Cells

Suitable prokaryotic cells include, but are not limited to, any of a variety of non-pathogenic laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302.

Suitable bacterial hosts include, but are not limited to, any of a variety of gram-positive, gram-negative, or gram-variable bacteria such as microorganisms belonging to the genera *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Rhodobacter, Rhodopseudomonas, Rhodospirillum, Scenedesmun, Strepromyces, Synnecoccus*, and *Zymomonas*. Examples of suitable host cell include *Escherichia coli, LactoBacillus* sp., *Lactococcus lactis, Salmonella* sp., *Salmonella enterica, Salmonella typhi, Salmonella typhimurium, Shigella* sp., *Shigella flexneri, Shigella sonnei, Shigella dysenteriae, Enterobacter sakazakii, Pseudomonas* sp. D-0110, *Pseudomonas pudica, Pseudomonas aeruginosa, Pseudomonas mevalonii, Rhodobacter sphaeroides, Rhodobacter capsulatus, Rhodospirillum rubrum, Rhodospirillum salexigens, Rhodospirillum salinarum, Rhodococcus* sp., *Mesorhizobium loti, Clostridium acetobutylicum, Clostridium tetani* E88, *Clostridium lituseburense, Clostridium saccharobutylicum, Clostridium perfringens, Clostridium beijerinckii, Fusobacterium nucleatum, Thermoanaerobacterium thermosaccharolyticum, Butyrivibrio fibrisolvens, Bacillus thuringiensis, Bacillus anthracis, Bacillus megaterium, Bacillus subtilis, Bacillus amyloliquefacines, LactoBacillus johnsonii, Acinetobacter, Roseburia* sp., *Faecalibacterium prausnitzii*, and *Coprococcus* sp., *Staphylococcus epidermidis, Staphylococcus haemolyticus, Staphylococcus aureus, Brevibacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratia ficaria, Serratia fonticola, Serratia liquefaciens, Serratia marcescens, Agrobacterium radiobacter, Agrobacterium rhizogenes, Agrobacterium rubi, Anabaena cylindrica, Anabaena doliolum, Anbaenaflos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophonniae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwnia ananas, Erwinia herbicola, Erwinia punctata, Erwinia terreus, Methylobacterium rhodesianum, Methylobacterium extorquens, Rhodopseudomonas blastica, Rhodopseudomonas marina, Rhodopseudomonas palustris, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis*, and the like (see, for example, Carrier et al. (1992) *J. Immunol.* 148:1176-1181; U.S. Pat. No. 6,447,784; and Sizemore et al. (1995) *Science* 270:299-302). Typically, the bacterium is a non-pathogenic strain.

Non-limiting examples of suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. In some embodiments, the host cell is *Escherichia coli*. Examples of *Escherichia coli* strains that can be employed include, but are not limited to, common cloning strains such as DH1, B, MG1655, W3110, BL21, DH10B, JM109, DH5alpha, XL1-Blue, XL2-Blue, MC1000, KY3276, W1485, HB101, No. 49, NY49, MP347, NM522, and derivatives thereof.

Where the genetically modified host cell is genetically modified version of a parent host cell that is a prokaryotic cell that does not normally produce IPP via a mevalonate pathway, in some embodiments, the one or more heterologous nucleic acids further comprise nucleotide sequences encoding a farnesyl pyrophosphate synthase. In some embodiments, the one or more heterologous nucleic acids further comprise nucleotide sequences encoding an IPP isomerase that is heterologous to the host cell. In some embodiments, the one or more heterologous nucleic acids further comprise nucleotide sequences encoding one or more mevalonate pathway enzymes. In some embodiments, the genetically modified host cell comprises a functional DXP pathway. In other embodiments, the genetically modified host cell comprises a functionally disabled DXP pathway. In some embodiments, the genetically modified host cell has a functionally disabled tryptophase A gene.

In some embodiments, a genetically modified prokaryotic host cell is genetically modified with one or more nucleic acids heterologous to the host cell, where the one or more heterologous nucleic acids comprise nucleotide sequences encoding: a) an amorphadiene synthase; b) an enzyme that oxidizes amorpha-4,11-diene to artemisinic-11,12-epoxide; and c) a farnesyl pyrophosphate synthase. In other embodiments, a genetically modified prokaryotic host cell is genetically modified with one or more nucleic acids heterologous to the host cell, where the one or more heterologous nucleic acids comprise nucleotide sequences encoding: a) an amorphadiene synthase; b) an enzyme that oxidizes amorpha-4,11-diene to artemisinic-11,12-epoxide; c) a farnesyl pyrophosphate synthase; and d) a heterologous IPP isomerase. In other embodiments, a genetically modified prokaryotic host cell is genetically modified with one or more nucleic acids heterologous to the host cell, where the one or more heterologous nucleic acids comprise nucleotide sequences encoding: a) an amorphadiene synthase; b) an enzyme that oxidizes amorpha-4,11-diene to artemisinic-11,12-epoxide; c) a farnesyl pyrophosphate synthase; d) a heterologous IPP isomerase; and e) one or more mevalonate pathway enzymes. In other embodiments, a genetically modified prokaryotic host cell is genetically modified with one or more nucleic acids heterologous to the host cell, where the one or more heterologous nucleic acids comprise nucleotide sequences encoding: a) an amorphadiene synthase; b) an enzyme that oxidizes amorpha-4,11-diene to artemisinic-11,12-epoxide; c) a farnesyl pyrophosphate synthase; d) a heterologous IPP isomerase; e) a mevalonate kinase; f) a phosphomevalonate kinase; and g) a mevalonate pyrophosphate decarboxylase. In other embodiments, a genetically modified prokaryotic host cell is genetically modified with one or more nucleic acids heterologous to the host cell, where the one or more heterologous nucleic acids comprise nucleotide sequences encoding: a) an amorphadiene synthase; b) an enzyme that oxidizes amorpha-4,11-diene to artemisinic-11,12-epoxide; c) a farnesyl pyrophosphate synthase; d) a heterologous IPP isomerase; e) an acetoacetyl-CoA thiolase; f) an HMG-CoA synthase; g) an HMG-CoA reductase; h) a mevalonate kinase; i) a phosphomevalonate kinase; and j) a mevalonate pyrophosphate decarboxylase. In some embodiments, the genetically modified host cell comprises a functional DXP pathway. In other embodiments, the genetically modified host cell comprises a functionally disabled DXP pathway. In some embodiments, the genetically modified host cell has a functionally disabled tryptophase A gene.

Nucleic Acids

A subject genetically modified host cell is generated by genetically modifying a parent host cell with one or more heterologous nucleic acids comprising nucleotide sequences encoding: a) an amorph-4,11-diene synthase; and b) an enzyme that oxidizes amorpha-4,11-diene to artemisinic-11, 12-epoxide. The one or more heterologous nucleic acids will in some embodiments further comprise nucleotide sequences encoding one or more additional enzymes, e.g. FPP synthase, IPP isomerase, one or more MEV pathway enzymes, one or more DXP pathway enzymes, etc.

Nucleotide Sequences Encoding an Enzyme that Catalyzes the Oxidation of amorpha-4,11-diene to artemisinic-11,12-epoxide A suitable nucleic acid comprises a nucleotide sequence that encodes an enzyme that catalyzes the oxidation of amorpha-4,11-diene to artemisinic-11,12-epoxide includes a nucleic acid comprising a nucleotide sequence that encodes a cytochrome P450 enzyme that lacks a transmembrane domain, such that the enzyme, when produced in a prokaryotic host cell, is produced in the cytosol and is soluble in the cytosol. The encoded enzyme is a single-chain polypeptide that includes at least two activities: 1) a cytochrome P450 enzyme that catalyzes oxidation of amorpha-4,11-diene to artemisinic-11,12-epoxide; and 2) a cytochrome P450 reductase (CPR).

A suitable nucleic acid comprises a nucleotide sequence that encodes an enzyme that catalyzes the oxidation of amorpha-4,11-diene to artemisinic-11,12-epoxide includes a nucleic acid comprising a nucleotide sequence that encodes an enzyme that catalyzes the oxidation of amorpha-4,11-diene such that at least about 85%, at least about 90%, at least about 95%, at least about 98%, at least about 99%, or greater than 99%, by weight or by molarity, of the product produced is artemisinic-11,12-epoxide. Thus, e.g., the amount of product other than artemisinic-11,12-epoxide, e.g., the amount of indigo, produced by the enzyme when provided with amorpha-4,11-diene as a substrate, is less than about 15%, less than about 10%, less than about 5%, less than about 2%, or less than about 1%, by weight or by molarity, of the total products produced.

In some embodiments, a suitable nucleic acid comprises the nucleotide sequence set forth in SEQ ID NO:4, or a variant of the sequence set forth in SEQ ID NO:4. In some embodiments, a suitable nucleic acid comprises a nucleotide sequence having at least about 75%, at least about 80%, at least about 85%, at least about 90%, at least about 95%, at least about 98%, at least about 99%, or greater, nucleotide sequence identity to the nucleotide sequence set forth in SEQ ID NO:4, with the proviso that the nucleotide sequence set forth in SEQ ID NO:2 (encoding wild-type $P450_{BM-3}$) is specifically excluded.

In some embodiments, the amino acid sequence of the cytochrome P450 differs from the amino acid sequence set forth in SEQ ID NO:1 by one amino acid, two amino acids, three amino acids, four amino acids, five amino acids, six amino acids, seven amino acids, eight amino acids, nine amino acids, ten amino acids, 10-15 amino acids, 15-20 amino acids, or more than 20 amino acids. Amino acid differences can include, e.g., substitutions, insertions, deletions, and additions. An exemplary nucleotide sequence encoding an enzyme that catalyzes the oxidation of amorpha-4,11-diene to artemisinic-11,12-epoxide is set forth in SEQ ID NO:4. The amino acid sequence set forth in SEQ ID NO:4 differs from the amino acid sequence set forth in SEQ ID NO:1 by an R47L substitution, a Y51F substitution, an F87A substitution, and an A328L substitution.

Also suitable for use is a nucleic acid comprising a nucleotide sequence encoding the amino acid sequence set forth in SEQ ID NO:3, or a variant of the amino acid sequence set forth in SEQ ID NO:3. The encoded amino acid sequence comprises at least amino acids corresponding to Leu-47, Phe-51, Ala-87, and Leu-328 of SEQ ID NO:3. In some embodiments, a suitable nucleic acid comprises a nucleotide sequence encoding an amino acid sequence having at least about 75%, at least about 80%, least about 85%, least about 90%, least about 95%, least about 98%, or least about 99% amino acid sequence identity to the amino acid sequence set forth in SEQ ID NO:3, where the enzyme comprises at least amino acids corresponding to Leu-47, Phe-51, Ala-87 and Leu-328 of SEQ ID NO:3, with the proviso that the encoded enzyme does not comprise the amino acid sequence set forth in SEQ ID NO:1. Thus, nucleotide sequences encoding the amino acid sequence set forth in SEQ ID NO:1 are specifically excluded.

In some embodiments, the nucleotide sequence encoding the cytochrome P450 enzyme is codon optimized for expression in, e.g., a prokaryotic host cell. SEQ ID NO:5 depicts a nucleotide sequence encoding a P450 enzyme having the amino acid sequence set forth in SEQ ID NO:1, where the nucleotide sequence is codon optimized for expression in a prokaryotic host cell such as E. coli.

Amorphadiene Synthase-encoding Nucleotide Sequences

An exemplary amorphadiene-synthase-encoding nucleotide sequence is set forth in SEQ ID NO:6. The coding sequence of an amorphadiene-synthase-encoding nucleotide sequence may be altered in various ways known in the art to generate targeted changes in the amino acid sequence of the encoded enzyme. The amino acid sequence of a variant amorphadiene synthase will in some embodiments be substantially similar to the amino acid sequence of an ADS encoded by the nucleotide sequence set forth in SEQ ID NO:6, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Also suitable for use is a nucleic acid comprising a nucleotide sequence having at least about 70%, at least about 75%, at least about 80%, at least about 85%, at least about 90%, at least about 95%, at least about 98%, or at least about 99% nucleotide sequence identity to SEQ ID NO:6.

FPP Synthase-encoding Nucleotide Sequences

Nucleotide sequences encoding FPP synthase are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836). See also WO 2006/014837 and U.S. Publication Nos. 2003/0148479, 2004/0005678, and 2006/0079476.

The coding sequence of any known FPP synthase may be altered in various ways known in the art to generate targeted changes in the amino acid sequence of the encoded enzyme. The amino acid sequence of a variant FPP synthase will in some embodiments be substantially similar to the amino acid sequence of any known FPP synthase, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Also suitable for use is a nucleic acid comprising a nucleotide sequence having at least about 70%, at least about 75%, at least about 80%, at least about 85%, at least about 90%, at least about 95%, at least about 98%, or at least about 99% nucleotide sequence identity to SEQ ID NO:7.

IPP Isomerase-encoding Nucleotide Sequences

Nucleotide sequences encoding IPP isomerase are known in the art. See, e.g., isopentenyl diphosphate:dimethylallyl diphosphate isomerase gene (J05090; *Saccharomyces cerevisiae*); Wang and Ohnuma (2000) *Biochim. Biophys. Acta* 1529:33-48; U.S. Pat. No. 6,645,747; GenBank Accession No. NM_121649 (*Arabidopsis thaliana*); U.S. Pat. No. 6,645,747; SEQ ID NO:1 of WO 02/095011; and SEQ ID NO:50 of WO 02/083720.

The coding sequence of any known IPP isomerase may be altered in various ways known in the art to generate targeted changes in the amino acid sequence of the encoded enzyme. The amino acid sequence of a variant IPP isomerase will in some embodiments be substantially similar to the amino acid sequence of any known IPP isomerase, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Also suitable for use is a nucleic acid comprising a nucleotide sequence having at least about 70%, at least about 75%, at least about 80%, at least about 85%, at least about 90%, at least about 95%, at least about 98%, or at least about 99% nucleotide sequence identity to SEQ ID NO:8.

MEV Pathway Enzyme-encoding Nucleotide Sequences

Nucleotide sequences encoding MEV pathway gene products are known in the art, and any known MEV pathway gene product-encoding nucleotide sequence can used to generate a genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), (AF082326; *Haematococcus pluvialis*), and (J05090; *Saccharomyces cerevisiae*). Nucleotide sequences encoding IDI can also be found in, e.g., Wang and Ohnuma (2000) *Biochim. Biophys. Acta* 1529:33-48; GenBank Accession No. NM_121649 (*Arabidopsis thaliana*); U.S. Pat. No. 6,645,747; SEQ ID NO:1 of WO 02/095011; and SEQ ID NO:50 of WO 02/083720.

In some embodiments, the HMGR coding region encodes a truncated form of HMGR ("tHMGR") that lacks the transmembrane domain of wild-type HMGR. The transmembrane domain of HMGR contains the regulatory portions of the enzyme and has no catalytic activity. See, e.g., GenBank Accession No. AX128213, providing the sequence encoding a truncated HMGR).

The coding sequence of any known MEV pathway enzyme may be altered in various ways known in the art to generate targeted changes in the amino acid sequence of the encoded enzyme. The amino acid sequence of a variant MEV pathway enzyme will in some embodiments be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Nucleotide sequences of expression constructs encoding one or more mevalonate pathway enzymes and/or amorphadiene synthase (ADS) are provided in U.S. Pat. No. 7,183,089, as follows: pBAD24MevT (SEQ ID NO:1; encoding an acetoacetyl-CoA thiolase, an HMGS, and an HMGR); pBAD33MevT (SEQ ID NO:2; encoding an acetoacetyl-CoA thiolase, an HMGS, and an HMGR); pMevT (SEQ ID NO:3; encoding an acetoacetyl-CoA thiolase, an HMGS, and an HMGR); pMBIS (SEQ ID NO:4; encoding MK, PMK, MPD, an isopentenyl pyrophosphate isomerase, and a farnesyl pyrophosphate synthase); pADS (SEQ ID NO:5; encoding ADS); pAtoB (SEQ ID NO:6; encoding acetoacetyl-CoA thiolase); pHMGS (SEQ ID NO:7; encoding HMGS); pHMGR (SEQ ID NO:8; encoding HMGR); and tHMGR (SEQ ID NO:13; encoding a truncated HMGR lacking the transmembrane domain of wild-type HMGR).

DXP Pathway Enzyme-encoding Nucleotide Sequences

Nucleotide sequences encoding DXP pathway enzymes are known in the art, and can be used in a subject method. Variants of any known nucleotide sequence encoding a DXP pathway enzyme can be used, where the encoded enzyme retains enzymatic activity. Variants of any known nucleotide sequence encoding a DXP pathway enzyme selected from 1-deoxy-D-xylulose-5-phosphate synthase (dxs); 1-deoxy-D-xylulose-5-phosphate reductoisomerase (IspC; dxr); 4-diphosphocytidyl-2-C-methyl-D-erythritol synthase (IspD; YbgP); 4-diphosphocytidyl-2-C-methyl-D-erythritol kinase (IspE; YchB); 2C-methyl-D-erythritol 2,4-cyclodiphosphate synthase (IspF; YbgB); and 1-hydroxy-2-methyl-2-(E)-butenyl 4-diphosphate synthase (IspG) can be used, where a variant differs in nucleotide sequence by one or more nucleotides from a reference sequence (e.g., a known sequence); and where a variant nucleotide sequence includes one or more nucleotide substitutions, insertions, truncations, or deletions, compared to a reference sequence, e.g., compared to a known sequence.

The coding sequence of any known DXP pathway enzyme may be altered in various ways known in the art to generate targeted changes in the amino acid sequence of the encoded enzyme. The amino acid of a variant DXP pathway enzyme will in some embodiments be substantially similar to the amino acid sequence of any known DXP pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Nucleotide sequences encoding 1-deoxy-D-xylulose-5-phosphate synthase (dxs) are known in the art. See, e.g., GenBank Accession No. DQ768815 (*Yersinia pestis* dxs); GenBank Accession No. AF143812 (*Lycopersicon esculentum* dxs); GenBank Accession No. Y18874 (*Synechococcus* PCC6301 dxs); GenBank Accession No. AF035440; *E. coli* dxs); GenBank Accession No. AF282878 (*Pseudomonas aeruginosa* dxs); GenBank Accession No. NM_121176 (*Arabidopsis thaliana* dxs); and GenBank Accession No. AB026631 (*Streptomyces* sp. CL190 dxs). Swissprot accession No. 078328 (*Capsicum annuum*). See also FIG. 5 of U.S. Patent Publication No. 2003/0219798 for nucleotide sequences encoding dxs.

Nucleotide sequences encoding 1-deoxy-D-xylulose-5-phosphate reductoisomerase (IspC; dxr) are known in the art. See, e.g., GenBank Accession No. AF282879 (*Pseudomonas aeruginosa* dxr); GenBank Accession No. AY081453 (*Arabidopsis thaliana* dxr); and GenBank Accession No. AJ297566 (*Zea mays* dxr). See also FIG. 31 of U.S. Patent Publication No. 2003/0219798 for nucleotide sequences encoding dxr.

Nucleotide sequences encoding 4-diphosphocytidyl-2-C-methyl-D-erythritol synthase (IspD; YbgP) are known in the art. See, e.g., GenBank Accession No. AF230737 (*Arabidopsis thaliana*); GenBank Accession No. CP000034.1 (nucleotides 2725605-2724895; *Shigella dysenteriae*); and GenBank Accession No. CP000036.1 (nucleotides 2780789 to 2781448; *Shigella boydii*). See also SEQ ID NO:5 of U.S. Pat. No. 6,660,507 (*Methylomonas* IspD).

Nucleotide sequences encoding 4-diphosphocytidyl-2-C-methyl-D-erythritol (IspE; YchB) kinase are known in the art. See, e.g., GenBank Accession No. CP000036.1 (nucleotides 1839782-1840633; *Shigella boydii*); GenBank Accession No. AF288615 (*Arabidopsis thaliana*) and GenBank Accession No. CP000266.1 (nucleotides 1272480-1271629; *Shigella flexneri*). See also, SEQ ID NO:7 of U.S. Pat. No. 6,660,507 (*Methylomonas* 16a IspE).

Nucleotide sequences encoding 2C-methyl-D-erythritol 2,4-cyclodiphosphate synthase (IspF; YbgB) are known in the art. See, e.g., GenBank Accession No. AE017220.1 (nucleotides 3025667-3025216; *Salmonella enterica* IspF); GenBank Accession No. NM_105070 (*Arabidopsis thaliana*); GenBank Accession No. AE014073.1 (nucleotides 2838621-283841; *Shigella flexneri*).

Nucleotide sequences encoding 1-hydroxy-2-methyl-2-(E)-butenyl 4-diphosphate synthase (IspG; GcpE) are known in the art. See, e.g., GenBank Accession No. CP000034.1 (nucleotides 2505082 to 2503964; *Shigella dysenteriae* IspG); GenBank Accession No. NM_180902 (*Arabidopsis thaliana*); GenBank Accession No. AE008814.1 (nucleotides 15609-14491; *Salmonella typhimurium* IsgG); GenBank Accession No. AE014613.1 (nucleotides 383225-384343; *Salmonella enterica* GcpE); GenBank Accession No. AE017220.1 (nucleotides 2678054-2676936; *Salmonella enterica* GcpE; and GenBank Accession No. BX95085.1 (nucleotides 3604460-3603539; *Erwinia carotova* GcpE).

IspH genes are known in the art. See, e.g., GenBank Accession No. AY168881 (*Arabidopsis thaliana*).

Nucleotide sequences having at least about 70%, at least about 75%, at least about 80%, at least about 85%, at least about 90%, at least about 95%, at least about 98%, at least about 99%, or higher, nucleotide sequence identity to a known nucleotide sequence encoding a DXP pathway enzyme are also suitable for use, where the nucleotide sequence encodes a functional DXP pathway enzyme.

Codon Usage

In some embodiments, a nucleotide sequence used to generate a subject genetically modified host cell for use in a subject method is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another example, in some embodiments, the nucleotide sequence will be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Expression Vectors

A subject genetically modified host cell is generated by genetically modifying a parent host cell with one or more heterologous nucleic acids comprising nucleotide sequences encoding: a) an amorph-4,11-diene synthase; and b) an enzyme that oxidizes amorpha-4,11-diene to artemisinic-11,12-epoxide. In some embodiments, the one or more heterologous nucleic acids comprises further nucleotide sequences encoding one or more additional enzymes, as discussed above.

In some embodiments, the heterologous nucleic acids are present in one or more expression vectors. In some embodiments, the heterologous nucleic acids are present in two or more separate expression vectors. For example, in some embodiments, heterologous nucleic acids comprising nucleotide sequences encoding ADS are present in a first expression vector; and at least the heterologous nucleic acid comprising a nucleotide sequence encoding the enzyme that oxidizes amorpha-4,11-diene to artemisinic-11,12-epoxide is present on a second expression vector. In other embodiments, heterologous nucleic acids comprising nucleotide sequences encoding the enzyme that oxidizes amorpha-4,11-diene to artemisinic-11,12-epoxide are present in a first expression vector; and one or more of the heterologous nucleic acids comprising nucleotide sequences encoding FPP synthase and ADS are present on a second expression vector. As another example, in some embodiments, heterologous nucleic acids comprising nucleotide sequences encoding the enzyme that oxidizes amorpha-4,11-diene to artemisinic-11,12-epoxide and the ADS are present in a first expression vector; and one or more of the heterologous nucleic acids comprising nucleotide sequences encoding FPP synthase and IPP isomerase are present on a second expression vector.

Where the genetically modified host cell is a prokaryote, multiple heterologous nucleotide sequences can be operably linked in a single operon within a vector, or can be provided as multiple operons in one or a plurality of vectors. For example, a single expression vector can comprise at least two, three, four, five, or all of the heterologous sequences encoding the entire mevalonate pathway enzymes, where the expression of each of the enzymes is present in one or more operons (e.g., two operons). Where desired, two expression vectors can be employed, each of which contains one or more heterologous sequences operably linked in a single operon.

In some embodiments, the nucleotide sequences encoding a) an amorph-4,11-diene synthase; and b) an enzyme that oxidizes amorpha-4,11-diene to artemisinic-11,12-epoxide are under transcriptional control of a single transcriptional control element. In other embodiments, the nucleotide sequences encoding a) an amorph-4,11-diene synthase; and b) an enzyme that oxidizes amorpha-4,11-diene to artemisinic-11,12-epoxide are under transcriptional control of two different transcriptional control elements. In some embodiments, additional nucleotide sequences encoding one or more additional enzymes are under transcriptional control of the same or different transcriptional control element as the transcriptional control element operably linked to the ADS-encoding sequence or the coding sequence for the enzyme that oxidizes amorpha-4,11-diene to artemisinic-11,12-epoxide. For example, in some embodiments, a nucleotide sequence encoding FPP synthase is included, and the FPP synthase-encoding nucleotide sequence and the ADS-encoding nucleotide sequence are under transcriptional control of a single transcriptional control element.

In some embodiments, the nucleotide sequences encoding a) one or more mevalonate pathway enzymes; b) an FPP synthase; c) an amorph-4,11-diene synthase; and d) an enzyme that oxidizes amorpha-4,11-diene to artemisinic-11,12-epoxide are under transcriptional control of a single transcriptional control element. In other embodiments, the nucleotide sequences encoding a) one or more mevalonate pathway enzymes; b) an FPP synthase; c) an amorph-4,11-diene synthase; and d) an enzyme that oxidizes amorpha-4,11-diene to artemisinic-11,12-epoxide are under transcriptional control of two or more different transcriptional control elements.

Where the host cell is a prokaryotic host cell that does not normally synthesize IPP via a mevalonate pathway, and where the one or more heterologous nucleic acids further comprises nucleotide sequences encoding one or more mevalonate pathway enzymes, in some embodiments, the nucleotide sequences encoding the one or more mevalonate pathway enzymes are under control of a first transcriptional control element; and nucleotide sequences encoding one or more of b) an FPP synthase; c) an amorph-4,11-diene synthase; and d) an enzyme that oxidizes amorpha-4,11-diene to artemisinic-11,12-epoxide are under transcriptional control of a second transcriptional control element. In other embodiments, e.g., where the one or more mevalonate pathway enzymes comprises an acetoacteyl-CoA thiolase, HMGS, HMGR, MK, PMK, and MPD, nucleotide sequences encoding the acetoacteyl-CoA thiolase, HMGS, and HMGR are under control of a first transcriptional control element; nucleotide sequences encoding the MK, PMK, and MPD are under control of a second transcriptional control element; and nucleotide sequences encoding one or more of b) an FPP synthase; c) an amorph-4,11-diene synthase; and d) an enzyme that oxidizes amorpha-4,11-diene to artemisinic-11,12-epoxide are under transcriptional control of a third transcriptional control element. Suitable transcriptional control elements include regulated (e.g., inducible) promoters and constitutive promoters.

Transcriptional Control Elements

Non-limiting examples of suitable eukaryotic promoters include CMV immediate early, HSV thymidine kinase, early and late SV40, LTRs from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the promoter is an inducible promoter. In some embodiments, the promoter is a constitutive promoter. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

In some embodiments, a promoter or other regulatory element(s) suitable for expression in a plant cell is used. Non-limiting examples of suitable constitutive promoters that are functional in a plant cell is the cauliflower mosaic virus 35S promoter, a tandem 35S promoter (Kay et al., *Science* 236: 1299 (1987)), a cauliflower mosaic virus 19S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell include, but are not limited to, a phenylalanine ammonia-lyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., *Cell* 55:705-717 (1988)); tetracycline and chlortetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject nucleic acid or a subject vector. Suitable tissue-selective regulatory elements, which can be used to ectopically express a nucleic acid in a single tissue or in a limited number of tissues, include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject nucleic acid into a plant host cell. Suitable vectors include, e.g., a Ti plasmid of *Agrobacterium tumefaciens* or an $Ri_1$ plasmid of *A. rhizogenes*. The Ti or $Ri_1$ plasmid is transmitted to plant cells on infection by *Agrobacterium* and is stably integrated into the plant genome. J. Schell, *Science*, 237: 1176-83 (1987). Also suitable for use is a plant artificial chromosome, as described in, e.g., U.S. Pat. No. 6,900,012.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagc promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25.)

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) J. Bacteriol. 177:4121-4130); a xylose-inducible promoter, for example, Pxyl (see, for example, Kim et al. (1996) Gene 181:71-76); a GAL1 promoter; a tryptophan promoter; a lac promoter; an alcohol-inducible promoter, for example, a methanol-inducible promoter, an ethanol-inducible promoter; a raffinose-inducible promoter; a heat-inducible promoter, for example, heat inducible lambda PL promoter; a promoter controlled by a heat-sensitive repressor (for example, C1857-repressed lambda-based expression vectors; see, for example, Hoffmann et al. (1999) *FEMS Microbiol Lett.* 177(2):327-34); and the like.

Expression Vectors

Suitable expression vectors include any of a variety of expression vectors available in the art; and variant and derivatives of such vectors. Those of ordinary skill in the art are familiar with selecting appropriate expression vectors for a given application. Numerous suitable expression vectors are known to those of skill in the art, and many are commercially available. Suitable expression vectors for use in constructing the subject host cells include, but are not limited to, baculovirus vectors, bacteriophage vectors, plasmids, phagemids, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. A typical expression vector contains an origin of replication that ensures propagation of the vector, a nucleic acid sequence that encodes a desired enzyme, and one or more regulatory elements that control the synthesis of the desired enzyme.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, an expression vector can be constructed to yield a desired level of copy numbers of the vector, and hence modulate the level of the encoded enzyme. In some embodiments, an expression vector provides for at least 10, between 10 to 20, between 20-50, between 50 and 100, or more than 100 copies of the expression vector in the host cell. Low copy number plasmids generally provide fewer than about 20 plasmid copies per cell; medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more than 200 plasmid copies per cell.

Suitable low-copy (centromeric) expression vectors for yeast include, but are not limited to, pRS415 and pRS416 (Sikorski & Hieter (1989) Genetics 122:19-27). In some embodiments, the enzyme-encoding sequences are present on one or more medium copy number plasmids. Medium copy number plasmids generally provide from about 20 plasmid copies per cell to about 50 plasmid copies per cell, or from about 20 plasmid copies per cell to about 80 plasmid copies per cell. Medium copy number plasmids for use in yeast include, e.g., Yep24. In some embodiments, the enzyme-encoding sequences are present on one or more high copy number plasmids. High copy number plasmids generally provide from about 30 plasmid copies per cell to about 200 plasmid copies per cell, or more. Suitable high-copy 2 micron expression vectors in yeast include, but are not limited to, pRS420 series vectors, e.g., pRS425 and pRS426 (Christianson et al. (1992) Gene 110:119-122).

Exemplary low copy expression vectors for use in prokaryotes such as *Escherichia coli* include, but are not limited to, pACYC184, pBeloBac11, pBR332, pBAD33, pBBR1MCS and its derivatives, pSC101, SuperCos (cosmid), and pWE15 (cosmid). Suitable medium copy expression vectors for use in prokaryotes such as *Escherichia coli* include, but are not limited to pTrc99A, pBAD24, and vectors containing a ColE1 origin of replication and its derivatives. Suitable high copy number expression vectors for use in prokaryotes such as *Escherichia coli* include, but are not limited to, pUC, pBluescript, pGEM, and pTZ vectors.

The level of translation of a nucleotide sequence in a genetically modified host cell can be altered in a number of ways, including, but not limited to, increasing the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence. Determination of preferred codons and rare codon tRNAs can be based on a survey of genes derived from the host cell.

The expression vector can also contain one or more selectable marker genes that, upon expression, confer one or more phenotypic traits useful for selecting or otherwise identifying host cells that carry the expression vector. Non-limiting examples of suitable selectable markers for prokaryotic cells include resistance to an antibiotic such as tetracycline, ampicillin, chloramphenicol, carbenicillin, or kanamycin.

In some embodiments, instead of antibiotic resistance as a selectable marker for the expression vector, a subject method will employ host cells that do not require the use of an antibiotic resistance conferring selectable marker to ensure plasmid (expression vector) maintenance. In these embodiments, the expression vector contains a plasmid maintenance system such as the 60-kb IncP (RK2) plasmid, optionally together with the RK2 plasmid replication and/or segregation system, to effect plasmid retention in the absence of antibiotic selection (see, for example, Sia et al. (1995) J. Bacteriol. 177: 2789-97; Pansegrau et al. (1994) J. Mol. Biol. 239:623-63). A suitable plasmid maintenance system for this purpose is encoded by the parDE operon of RK2, which codes for a stable toxin and an unstable antitoxin. The antitoxin can inhibit the lethal action of the toxin by direct protein-protein interaction. Cells that lose the expression vector that harbors the parDE operon are quickly deprived of the unstable antitoxin, resulting in the stable toxin then causing cell death. The RK2 plasmid replication system is encoded by the trfA gene, which codes for a DNA replication protein. The RK2 plasmid segregation system is encoded by the parCBA operon, which codes for proteins that function to resolve plasmid multimers that may arise from DNA replication.

To generate a genetically modified host cell, one or more heterologous nucleic acids is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like.

Further Genetic Modifications

In some embodiments, the genetically modified host cell comprises one or more additional genetic modifications.

Further Genetic Modifications of Eukaryotic Host Cells

In some embodiments, a genetically modified eukaryotic host cell further comprises one or more genetic modifications that provide for one or more of: a) increased prenyltransferase activity levels; and b) decreased squalene synthase levels.

In some embodiments, a genetically modified eukaryotic host cell is further genetically modified such that the level of geranyl diphosphate synthase (GPPS) and/or farnesyl diphosphate synthase (FPPS) activity is increased. See, e.g., WO 2006/014837.

In some embodiments, a genetically modified eukaryotic host cell further comprises one or more genetic modifications that provide for decreased squalene synthase levels. The enzyme squalene synthase catalyzes a reaction that converts farnesyl diphosphate into squalene. This step is the first step in the pathway leading from farnesyl diphosphate to ergosterol. Thus by limiting the action of this enzyme, FPP is shunted towards terpenoid production pathways utilizing, e.g., terpene synthases or GGPP synthase and subsequent terpene synthases. See, e.g., WO 2006/014837.

In other embodiments, a genetically modified eukaryotic host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, a genetically modified eukaryotic host cell is one that is genetically modified to include one or more nucleic acids comprising a nucleotide sequence(s) that encode DXP biosynthetic pathway gene product(s); and nucleotide sequences encoding flavodoxin and a corresponding flavodoxin reductase. Nucleotide sequences encoding flavodoxin and flavodoxin reductases are known in the art, and any known sequence, or variant thereof, that encodes a flavodoxin or flavodoxin reductase can be used. See, e.g., GenBank Accession No. CP00034 (nucleotides 586626-586096; *Shigella flexneri* flavodoxin); GenBank Accession No. CP000038.1 (nucleotides 674404-673874; *Shigella sonnei* flavodoxin); GenBank Accession No. AE017220.1 (nucleotides 799550-799066; *Salmonella enterica*); GenBank Accession No. U67169 (*Klebsiella pneumoniae* flavodoxin; fldA); and GenBank Accession No. AL590842.1 (nucleotides 2964901-2964468; *Yersinia pestis* flavodoxin). See, e.g., GenBank Accession No. CP000266.1 (nucleotides 4100732-4099986; *Shigella flexneri* flavodoxin reductase); GenBank Accession No. CP000038.1 (nucleotides 4328513-4327767; *Salmonella sonnei* flavodoxin reductase); and GenBank Accession No. AE017220.1 (nucleotides 4226162-4225639 flavodoxin reductase).

Further Genetic Modifications of Prokaryotic Host Cells

In some embodiments, a genetically modified prokaryotic host cell is one that does not normally synthesize IPP via a mevalonate pathway, and is genetically modified to include one or more nucleic acids comprising a nucleotide sequence(s) that encode MEV biosynthetic pathway gene product(s); and is further genetically modified such that an endogenous DXP biosynthetic pathway gene is functionally disabled.

In some embodiments, where subject genetically modified host cell is a prokaryotic host cell that is genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

In some embodiments, a genetically modified prokaryotic host cell comprises a functionally disabled endogenous tryptophanase A gene. An endogenous tryptophanase gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Variant P450 Enzymes

The present invention provides a variant P450 enzyme that catalyzes the oxidation of amorpha-4,11-diene to generate artemisinic-11,12-epoxide. A subject P450 variant lacks a transmembrane domain, such that the enzyme, when produced in a prokaryotic host cell, is produced in the cytosol and is soluble in the cytosol, e.g., is not membrane-associated. A subject variant P450 enzyme is a single-chain polypeptide that includes at least two activities: 1) a cytochrome P450 enzyme that catalyzes oxidation of amorpha-4,11-diene to artemisinic-11,12-epoxide; and 2) a cytochrome P450 reductase (CPR).

A subject variant P450 enzyme catalyzes the oxidation of amorpha-4,11-diene to generate artemisinic-11,12-epoxide, such that at least about 85%, at least about 90%, at least about 95%, at least about 98%, or at least about 99%, or greater than 99%, of the product produced is artemisinic-11,12-epoxide.

A subject variant P450 enzyme catalyzes the oxidation of amorpha-4,11-diene to generate artemisinic-11,12-epoxide without production of a substantial amount of side products, e.g., without substantial production of products other than artemisinic-11,12-epoxide, where side products may include indigo. Thus, in some embodiments, products produced by action of a subject variant P450 enzyme, when provided with amorpha-4,11-diene as substrate, comprise at least about 85%, at least about 90%, at least about 95%, at least about 98%, at least about 99%, or greater than 99%, by weight or molarity, artemisinic-11,12-epoxide, and less than about 15%, less than about 10%, less than about 5%, less than about 2%, less than about 1%, or less than about 1%, by weight or by molarity, of a product other than artemisinic-11,12-epoxide.

A subject variant P450 enzyme catalyzes production of artemisinic-11,12-epoxide at high levels when present in a prokaryotic host cell that has been genetically modified with heterologous nucleic acids encoding at least MK, PMK, MPD, FPP synthase, and ADS. A subject variant P450 enzyme catalyzes production of artemisinic-11,12-epoxide at levels greater than 400 mg/L when present in a prokaryotic host cell that has been genetically modified to produce IPP via the mevalonate pathway, where the host cell has also been genetically modified to produce FPP synthase and ADS. For example, a subject variant P450 enzyme catalyzes production of artemisinic-11,12-epoxide in an amount of greater than 400 mg/L, e.g., at least about 450 mg/L, at least about 500 mg/L, at least about 600 mg/L, at least about 700 mg/L, at least about 800 mg/L, at least about 900 mg/L, at least about 1000 mg/L, at least about 1250 mg/L, at least about 1500 mg/L, at least about 2000 mg/L, or more than about 2000 mg/L, when present in a genetically modified host cell that has been genetically modified to produce MK, PMK, MPD, heterologous IPP isomerase, FPP synthase, and ADS, where the genetically modified host cell is cultured in a culture medium comprising mevalonate. As another example, a subject variant P450 enzyme catalyzes production of artemisinic-11,12-epoxide in an amount of greater than 400 mg/L, e.g., at least about 450 mg/L, at least about 500 mg/L, at least about 600 mg/L, at least about 700 mg/L, at least about 800 mg/L, at least about 900 mg/L, at least about 1000 mg/L, at least about 1250 mg/L, at least about 1500 mg/L, at least about 2000 mg/L, or more than about 2000 mg/L, when present in a genetically modified host cell that has been genetically modified to produce acetoacetyl-CoA thiolase, HMGS, HMGR, MK, PMK, MPD, a heterologous IPP isomerase, FPP synthase, and ADS, where the genetically modified host cell is cultured in a suitable culture medium.

Whether a variant P450 enzyme is capable of catalyzing production of artemisinic-11,12-epoxide at levels greater than 450 mg/L can be readily determined by introducing into a host cell a nucleic acid comprising a nucleotide sequence encoding a variant P450 enzyme, where the host cell has been genetically modified to produce acetoacetyl-CoA thiolase, HMGS, HMGR, MK, PMK, MPD, a heterologous IPP isomerase, FPP synthase, and ADS, where the genetically modified host cell is cultured in a suitable culture medium. A suitable host cell for this purpose is described in the Example.

In some embodiments, a subject variant P450 enzyme comprises at least amino acids corresponding to Leu-47, Phe-51, Ala-87, and Leu-328 of SEQ ID NO:3. In some embodiments, a subject variant P450 enzyme comprises an amino acid sequence having at least about 75%, at least about 80%, least about 85%, least about 90%, least about 95%, least about 98%, or least about 99% amino acid sequence identity to the amino acid sequence set forth in SEQ ID NO:3, where the enzyme comprises at least amino acids corresponding to Leu-47, Phe-51, Ala-87 and Leu-328 of SEQ ID NO:3, with the proviso that the enzyme does not comprise the amino acid sequence set forth in SEQ ID NO:1. The amino acid sequence of a variant P450 pathway enzyme will in some embodiments be substantially similar to the amino acid sequence set forth in SEQ ID NO:3, e.g., will differ by at least one amino acid, and may differ by at least two, at least 5, at least 10, or at least 20 amino acids, but typically not more than about fifty amino acids. The sequence changes may be substitutions, insertions or deletions. One or more amino acid differences can be introduced that result in conservative amino acid changes in the variant P450 enzyme, relative to the amino acid sequence set forth in SEQ ID NO:3. In some embodiments, a subject variant P450 enzyme comprises the amino acid sequence set forth in SEQ ID NO:3.

In some embodiments, a subject variant P450 enzyme is a fusion protein, where the fusion protein includes the variant P450 enzyme fused in-frame to a heterologous protein, e.g., a protein other than the variant P450 enzyme, where the heterologous protein is also referred to as a "fusion partner." In some embodiments, the fusion partner is linked to the variant P450 enzyme at the N-terminus of the variant P450 enzyme. In other embodiments, the fusion partner is linked at the C-terminus of the variant P450 enzyme. In other embodiments, the fusion partner is internal to the variant P450 enzyme.

Suitable fusion partners include, but are not limited to, epitope tags; solubilization domains; and polypeptides that provide a detectable signal (e.g., fluorescent proteins; chromogenic proteins; enzymes that generate luminescent, fluorescent, or chromogenic products; and the like).

The present invention further provides compositions comprising a subject variant P450 enzyme. Compositions comprising a subject variant P450 enzyme will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Variant P450 Nucleic Acids

The present invention further provides nucleic acids comprising nucleotide sequence encoding a subject variant P450 enzyme, as well as vector and host cells comprising the nucleic acids. A nucleic acid comprising a nucleotide sequence encoding a subject variant P450 enzyme is referred to herein as a "variant P450 nucleic acid."

In some embodiments, a subject variant P450 nucleic acid comprises the nucleotide sequence set forth in SEQ ID NO:4, or a variant of the sequence set forth in SEQ ID NO:4. In some embodiments, a subject variant P450 nucleic acid comprises a nucleotide sequence having at least about 75%, at least about 80%, at least about 85%, at least about 90%, at least about 95%, at least about 98%, at least about 99%, or greater, nucleotide sequence identity to the nucleotide sequence set forth in SEQ ID NO:4, with the proviso that the nucleotide sequence set forth in SEQ ID NO:2 is specifically excluded. An exemplary nucleotide sequence encoding an enzyme that catalyzes the oxidation of amorpha-4,11-diene to artemisinic-11,12-epoxide is set forth in SEQ ID NO:4.

In some embodiments, a subject variant P450 nucleic acid comprises a nucleotide sequence encoding the amino acid sequence set forth in SEQ ID NO:3, or a variant of the amino acid sequence set forth in SEQ ID NO:3. The encoded amino acid sequence comprises at least amino acids corresponding to Leu-47, Phe-51, Ala-87, and Leu-328 of SEQ ID NO:3. In some embodiments, a subject variant P450 nucleic acid comprises a nucleotide sequence encoding an amino acid sequence having at least about 75%, at least about 80%, least about 85%, least about 90%, least about 95%, least about 98%, or least about 99% amino acid sequence identity to the amino acid sequence set forth in SEQ ID NO:3, where the enzyme comprises at least amino acids corresponding to Leu-47, Phe-51, Ala-87 and Leu-328 of SEQ ID NO:3, with the proviso that the encoded enzyme does not comprise the amino acid sequence set forth in SEQ ID NO:1. Thus, nucleotide sequences encoding the amino acid sequence set forth in SEQ ID NO:1 are specifically excluded.

In other embodiments, a subject variant P450 nucleic acid hybridizes under stringent hybridization conditions with a nucleic acid having the nucleotide sequence set forth in SEQ ID NO:4, where the variant P450 nucleic acid encodes a P450 enzyme that comprises at least amino acids corresponding to Leu-47, Phe-51, Ala-87, and Leu-328 of SEQ ID NO:3, with the proviso that the nucleotide sequence set forth SEQ ID NO:2 is specifically excluded.

In some embodiments, a subject variant P450 enzyme-encoding nucleotide sequence is present in an expression cassette, e.g., the variant P450 enzyme-encoding nucleotide sequence is operably linked to one or more of a promoter, a transcription termination signal, and a translation termination signal. In some embodiments, a subject variant P450 enzyme-encoding nucleotide sequence is operably linked to one or more control elements. For example, in some embodiments, a subject variant P450 enzyme-encoding nucleotide sequence is operably linked to a transcriptional control element. Suitable transcriptional control elements include regulated (e.g., inducible) promoters and constitutive promoters.

Control Elements

Non-limiting examples of suitable eukaryotic promoters include CMV immediate early, HSV thymidine kinase, early and late SV40, LTRs from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the promoter is an inducible promoter. In some embodiments, the promoter is a constitutive promoter. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

In some embodiments, a promoter or other regulatory element(s) suitable for expression in a plant cell is used. Non-limiting examples of suitable constitutive promoters that are functional in a plant cell is the cauliflower mosaic virus 35S promoter, a tandem 35S promoter (Kay et al., *Science* 236: 1299 (1987)), a cauliflower mosaic virus 19S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell include, but are not limited to, a phenylalanine ammonia-lyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., *Cell* 55:705-717 (1988)); tetracycline and chlortetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject nucleic acid or a subject vector. Suitable tissue-selective regulatory elements, which can be used to ectopically express a nucleic acid in a single tissue or in a limited number of tissues, include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject nucleic acid into a plant host cell. Suitable vectors include, e.g., a Ti plasmid of *Agrobacterium tumefaciens* or an $Ri_1$ plasmid of *A. rhizogenes*. The Ti or $Ri_1$ plasmid is transmitted to plant cells on infection by *Agrobacterium* and is stably integrated into the plant genome. J. Schell, *Science,* 237: 1176-83 (1987). Also suitable for use is a plant artificial chromosome, as described in, e.g., U.S. Pat. No. 6,900,012.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagc promoter (Pulkkinen and Miller, *J. Bacteriol.,* 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (Lacd repressor protein changes conformation when contacted with lactose, thereby preventing the Lacd repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25.)

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) J. Bacteriol. 177:4121-4130); a xylose-inducible promoter, for example, Pxyl (see, for example, Kim et al. (1996) Gene 181:71-76); a GAL1 promoter; a tryptophan promoter; a lac promoter; an alcohol-inducible promoter, for example, a methanol-inducible promoter, an ethanol-inducible promoter; a raffinose-inducible promoter; a heat-inducible promoter, for example, heat inducible lambda PL promoter; a promoter controlled by a heat-sensitive repressor (for example, C1857-repressed lambda-based expression vectors; see, for example, Hoffmann et al. (1999) *FEMS* Microbiol Lett. 177(2):327-34); and the like.

Recombinant Vectors

In some embodiments, a subject variant P450 nucleic acid is present in a recombinant construct (also referred to as a "recombinant vector"), which recombinant vector can provide for propagation and/or expression of the variant P450 nucleic acid in a suitable host cell or in a cell-free transcription/translation system. Recombinant constructs that provide for expression of the variant P450 nucleic acid are referred to as "expression vectors."

Suitable expression vectors include any of a variety of expression vectors available in the art; and variant and derivatives of such vectors. Those of ordinary skill in the art are familiar with selecting appropriate expression vectors for a given application. Numerous suitable expression vectors are known to those of skill in the art, and many are commercially available. Suitable expression vectors include, but are not limited to, baculovirus vectors, bacteriophage vectors, plasmids, phagemids, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. A typical expression vector contains an origin of replication that ensures propagation of the vector, a nucleic acid sequence that encodes a variant P450 enzyme, and one or more regulatory elements that control the synthesis of the variant P450 enzyme.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, an expression vector can be constructed to yield a desired level of copy numbers of the vector, and hence modulate the level of the encoded variant P450 enzyme. In some embodiments, an expression vector provides for at least 10, between 10 to 20, between 20-50, between 50 and 100, or more than 100 copies of the expression vector in the host cell. Low copy number plasmids generally provide fewer than about 20 plasmid copies per cell; medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more than 200 plasmid copies per cell.

Suitable low-copy (centromeric) expression vectors for yeast include, but are not limited to, pRS415 and pRS416 (Sikorski & Hieter (1989) Genetics 122:19-27). In some embodiments, the enzyme-encoding sequences are present on one or more medium copy number plasmids. Medium copy number plasmids generally provide from about 20 plasmid copies per cell to about 50 plasmid copies per cell, or from about 20 plasmid copies per cell to about 80 plasmid copies per cell. Medium copy number plasmids for use in yeast include, e.g., Yep24. In some embodiments, the enzyme-encoding sequences are present on one or more high copy number plasmids. High copy number plasmids generally provide from about 30 plasmid copies per cell to about 200 plasmid copies per cell, or more. Suitable high-copy 2 micron expression vectors in yeast include, but are not limited to, pRS420 series vectors, e.g., pRS425 and pRS426 (Christianson et al. (1992) Gene 110:119-122).

Exemplary low copy expression vectors for use in prokaryotes such as *Escherichia coli* include, but are not limited to, pACYC184, pBeloBac11, pBR332, pBAD33, pBBR1MCS and its derivatives, pSC11, SuperCos (cosmid), and pWE15 (cosmid). Suitable medium copy expression vectors for use in prokaryotes such as *Escherichia coli* include, but are not limited to pTrc99A, pBAD24, and vectors containing a ColE1 origin of replication and its derivatives. Suitable high copy number expression vectors for use in prokaryotes such as *Escherichia coli* include, but are not limited to, pUC, pBluescript, pGEM, and pTZ vectors.

The level of translation of a nucleotide sequence in a genetically modified host cell can be altered in a number of ways, including, but not limited to, increasing the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence. Determination of preferred codons and rare codon tRNAs can be based on a survey of genes derived from the host cell.

The expression vector can also contain one or more selectable marker genes that, upon expression, confer one or more phenotypic traits useful for selecting or otherwise identifying host cells that carry the expression vector. Non-limiting examples of suitable selectable markers for prokaryotic cells include resistance to an antibiotic such as tetracycline, ampicillin, chloramphenicol, carbenicillin, or kanamycin.

In some embodiments, instead of antibiotic resistance as a selectable marker for the expression vector, a subject method will employ host cells that do not require the use of an antibiotic resistance conferring selectable marker to ensure plasmid (expression vector) maintenance. In these embodiments, the expression vector contains a plasmid maintenance system such as the 60-kb IncP (RK2) plasmid, optionally together with the RK2 plasmid replication and/or segregation system, to effect plasmid retention in the absence of antibiotic selection (see, for example, Sia et al. (1995) *J. Bacteriol.* 177: 2789-97; Pansegrau et al. (1994) *J. Mol. Biol.* 239:623-63). A suitable plasmid maintenance system for this purpose is encoded by the parDE operon of RK2, which codes for a stable toxin and an unstable antitoxin. The antitoxin can inhibit the lethal action of the toxin by direct protein-protein interaction. Cells that lose the expression vector that harbors the parDE operon are quickly deprived of the unstable antitoxin, resulting in the stable toxin then causing cell death. The RK2 plasmid replication system is encoded by the trfA gene, which codes for a DNA replication protein. The RK2 plasmid segregation system is encoded by the parCBA operon, which codes for proteins that function to resolve plasmid multimers that may arise from DNA replication.

To generate a genetically modified host cell, one or more heterologous nucleic acids is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like.

Genetically Modified Host Cells

The present invention further provides genetically modified host cells. In some embodiments, a subject genetically modified host cell comprises a subject variant P450 nucleic acid is useful for producing the encoded variant P450 enzyme. In other embodiments, a subject genetically modified host cell comprises a subject variant P450 nucleic acid is useful for producing artemisinic-11,12-epoxide, where production of the encoded variant P450 enzyme provides for oxidation of amorpha-4,11-diene to artemisinic-11,12-epoxide, such that the genetically modified host cell produces artemisinic-11,12-epoxide.

In some embodiments, a subject genetically modified host cell comprises one or more nucleic acids heterologous to the host cell, where the one or more nucleic acids comprise nucleotide sequences encoding: a) a subject variant P450 enzyme, as well as one or more of: i) an amorphadiene synthase; ii) an FPP synthase; iii) an IPP isomerase; and iv) one or more mevalonate pathway enzymes.

In other embodiments, a subject genetically modified host cell comprises one or more nucleic acids heterologous to the host cell, where the one or more nucleic acids comprise nucleotide sequences encoding: a) a subject variant P450 enzyme, as well as one or more of: i) an amorphadiene synthase; ii) an FPP synthase; iii) an IPP isomerase; and iv) one or more DXP pathway enzymes.

Genetically Modified Host Cells Comprising a Variant P450 Nucleic Acid

In some embodiments, a subject genetically modified host cell comprises a subject variant P450 nucleic acid. In some embodiments, a subject genetically modified host cell is a genetically modified version of a parent cell that does not normally produce artemisinic epoxide or artemisinin. In some embodiments, the parent host cell is a eukaryotic host cell that does not normally produce artemisinic epoxide or artemisinin. In other embodiments, the parent cell is a prokaryotic host cell that does not normally produce artemisinic epoxide or artemisinin. In some embodiments, the parent cell is a prokaryotic host cell that does not normally synthesize isopentenyl pyrophosphate (IPP) via a mevalonate pathway.

In some embodiments, a subject genetically modified host cell is a unicellular organism, or is grown in culture as single cells. In some embodiments, a subject genetically modified host cell is an in vitro host cell. In other embodiments, a subject genetically modified host cell is an in vivo host cell.

Eukaryotic Host Cells

In some embodiments, a subject genetically modified host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a eukaryotic cell other than a plant cell.

In other embodiments, a subject genetically modified host cell is a plant cell. Plant cells include cells of monocotyledons ("monocots") and dicotyledons ("dicots").

Where a subject genetically modified host cell is a genetically modified version of a parent eukaryotic cell that does not normally synthesize artemisinic epoxide or artemisinin, in some embodiments, a subject genetically modified host cell comprises, in addition to a subject variant P450 nucleic acid, one or more heterologous nucleic acids comprising a nucleotide sequence encoding a farnesyl pyrophosphate synthase, e.g., an FPP synthase that is heterologous to the host cell. In some embodiments, a subject genetically modified host cell comprises, in addition to a subject variant P450 nucleic acid, one or more heterologous nucleic acids comprising a nucleotide sequence encoding an IPP isomerase, e.g., an IPP isomerase that is heterologous to the host cell. In some embodiments, a subject genetically modified host cell comprises, in addition to a subject variant P450 nucleic acid, one or more heterologous nucleic acids comprising a nucleotide sequence encoding one or more DXP pathway enzymes.

Prokaryotic Host Cells

Suitable prokaryotic cells include, but are not limited to, any of a variety of non-pathogenic laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302.

Suitable bacterial hosts include, but are not limited to, any of a variety of gram-positive, gram-negative, or gram-variable bacteria such as microorganisms belonging to the genera *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Rhodobacter, Rhodopseudomonas, Rhodospirillum, Scenedesmun, Strepromyces, Synnecoccus*, and *Zymomonas*. Examples of suitable host cell include *Escherichia coli, LactoBacillus* sp., *Lactococcus lactis, Salmonella* sp., *Salmonella enterica, Salmonella typhi, Salmonella typhimurium, Shigella* sp., *Shigella flexneri, Shigella sonnei, Shigella dysenteriae, Enterobacter sakazakii, Pseudomonas* sp. D-0110, *Pseudomonas pudica, Pseudomonas aeruginosa, Pseudomonas mevalonii, Rhodobacter sphaeroides, Rhodobacter capsulatus, Rhodospirillum rubrum, Rhodospirillum salexigens, Rhodospirillum salinarum, Rhodococcus* sp., *Mesorhizobium loti, Clostridium acetobutylicum, Clostridium tetani* E88, *Clostridium lituseburense, Clostridium saccharobutylicum, Clostridium perfringens, Clostridium beijerinckii, Fusobacterium nucleatum, Thermoanaerobacterium thermosaccharolyticum, Butyrivibrio fibrisolvens, Bacillus thuringiensis, Bacillus anthracis, Bacillus megaterium, Bacillus subtilis, Bacillus amyloliquefacines, LactoBacillus johnsonii, Acinetobacter, Roseburia* sp., *Faecalibacterium prausnitzii*, and *Coprococcus* sp., *Staphylococcus epidermidis, Staphylococcus haemolyticus, Staphylococcus aureus, Brevibacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratiaficaria, Serratiafonticola, Serratia liquefaciens, Serratia marcescens, Agrobacterium radiobacter, Agrobacterium rhizogenes, Agrobacterium rubi, Anabaena cylindrica, Anabaena doliolum, Anbaenaflos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophonniae, Arthrobacter roseoparaffinus, Arthrobacter sulfureus, Arthrobacter ureafaciens, Chromatium buderi, Chromatium tepidum, Chromatium vinosum, Chromatium warmingii, Chromatiumfluviatile, Erwinia uredovora, Erwinia carotovora, Erwnia ananas, Erwinia herbicola, Erwinia punctata, Erwinia terreus, Methylobacterium rhodesianum, Methylobacterium extorquens, Rhodopseudomonas blastica, Rhodopseudomonas marina, Rhodopseudomonas palustris, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis*, and the like (see, for example, Carrier et al. (1992) J. Immunol. 148:1176-1181; U.S. Pat. No. 6,447,784; and Sizemore et al. (1995) Science 270:299-302). Typically, the bacterium is a non-pathogenic strain.

Non-limiting examples of suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. In some embodiments, the host cell is *Escherichia coli*. Examples of *Escherichia coli* strains that can be employed include, but are not limited to, common cloning strains such as DH1, B, MG1655, W3110, BL21, DH10B, JM109, DH5alpha, XL1-Blue, XL2-Blue, MC1000, KY3276, W1485, HB101, No. 49, NY49, MP347, NM522, and derivatives thereof.

Where a subject genetically modified host cell is a genetically modified version of a parent host cell that is a prokaryotic cell that does not normally produce IPP via a mevalonate pathway, in some embodiments, a subject genetically modified host cell comprises, in addition to a variant P450 nucleic acid, one or more heterologous nucleic acids comprising nucleotide sequences encoding a farnesyl pyrophosphate synthase. In some embodiments, a subject genetically modified host cell comprises, in addition to a variant P450 nucleic acid, one or more heterologous nucleic acids comprising nucleotide sequences encoding an IPP isomerase that is heterologous to the host cell. In some embodiments, a subject genetically modified host cell comprises, in addition to a variant P450 nucleic acid, one or more heterologous nucleic acids comprising nucleotide sequences encoding one or more mevalonate pathway enzymes. In some embodiments, a subject genetically modified host cell comprises a functional DXP pathway. In other embodiments, a subject genetically modified host cell comprises a functionally disabled DXP pathway. In some embodiments, a subject genetically modified host cell has a functionally disabled tryptophase A gene.

In some embodiments, a subject genetically modified prokaryotic host cell a subject genetically modified host cell comprises, in addition to a variant P450 nucleic acid, one or more heterologous nucleic acids comprising nucleotide sequences encoding: i) an ADS; and ii) a farnesyl pyrophosphate synthase. In other embodiments, a subject genetically modified prokaryotic host cell a subject genetically modified host cell comprises, in addition to a variant P450 nucleic acid, one or more heterologous nucleic acids comprising nucleotide sequences encoding: i) an ADS; ii) a farnesyl pyrophosphate synthase; and iii) a heterologous IPP isomerase. In other embodiments, a subject genetically modified prokaryotic host cell a subject genetically modified host cell comprises, in addition to a variant P450 nucleic acid, one or more heterologous nucleic acids comprising nucleotide sequences encoding: i) an ADS; ii) a farnesyl pyrophosphate synthase; iii) a heterologous IPP isomerase; and iv) one or more mevalonate pathway enzymes. In other embodiments, a subject genetically modified prokaryotic host cell a subject genetically modified host cell comprises, in addition to a variant P450 nucleic acid, one or more heterologous nucleic acids comprising nucleotide sequences encoding: i) an ADS; ii) a farnesyl pyrophosphate synthase; iii) a heterologous IPP isomerase; iv) a mevalonate kinase; v) a phosphomevalonate kinase; and vi) a mevalonate pyrophosphate decarboxylase. In other embodiments, a subject genetically modified prokaryotic host cell a subject genetically modified host cell comprises, in addition to a variant P450 nucleic acid, one or more heterologous nucleic acids comprising nucleotide sequences encoding: i) an ADS; ii) a farnesyl pyrophosphate synthase; iii) a heterologous IPP isomerase; iv) an acetoacetyl-CoA thiolase; v) an HMG-CoA synthase; vi) an HMG-CoA reductase; vii) a mevalonate kinase; viii) a phosphomevalonate kinase; and ix) a mevalonate pyrophosphate decarboxylase. In some embodiments, a subject genetically modified prokaryotic host cell comprises a functional DXP pathway. In other embodiments, a subject genetically modified prokaryotic host cell comprises a functionally disabled DXP pathway. In some embodiments, a subject genetically modified prokaryotic host cell has a functionally disabled tryptophase A gene.

Generating a Genetically Modified Host Cell

To generate a subject genetically modified host cell, a variant P450 nucleic acid, and optionally additional nucleic acids, is introduced stably or transiently into a parent host cell, using established techniques, including, but not limited to, electroporation, calcium phosphate precipitation, DEAE-dextran mediated transfection, liposome-mediated transfection, and the like.

Producing a Variant P450 Enzyme

To produce a subject variant P450 enzyme, a subject genetically modified host cell is cultured in a suitable medium under conditions that permit transcription and translation of the variant P450 nucleic acid. In some embodiments, the variant P450 enzyme is recovered from the cell. In some embodiments, the variant P450 enzyme is isolated, and will in some embodiments be purified using, e.g., standard protein purification methods.

Genetically Modified Host Cells Comprising One or More Heterologous Nucleic Acids Encoding Two or More Enzymes As noted above, in some embodiments, a subject genetically modified host cell comprises one or more nucleic acids heterologous to the host cell, where the one or more nucleic acids comprise nucleotide sequences encoding a subject variant P450 enzyme, and one or more additional enzymes that, together with the variant P450 enzyme, provide for production of artemisinic-11,12-epoxide by the genetically modified host cell.

In some embodiments, a subject genetically modified host cell, when cultured under appropriate culture conditions, produces artemisinic-11,12-epoxide in an amount of greater than 400 mg/L. For example, in some embodiments, the amount of artemisinic epoxide produced by a subject genetically modified host cell, e.g., in a culture of a subject genetically modified host cell, is from about 400 mg/L to about 450 mg/L, from about 450 mg/L to about 500 mg/L, from about 500 mg/L to about 750 mg/L, from about 750 mg/L to about 1000 mg/L, from about 1000 mg/L to about 1250 mg/L, from about 1250 mg/L to about 1500 mg/L, from about 1500 mg/L to about 1750 mg/L, from about 1750 mg/L to about 2000 mg/L, from about 2000 mg/L to about 2500 mg/L, from about 2500 mg/L to about 3000 mg/L, from about 3000 mg/L to about 4000 mg/L, or from about 4000 mg/L to about 5000 mg/L, or greater than 5000 mg/L. Production levels are expressed on a per unit volume (e.g., per liter) cell culture basis.

In some embodiments, a subject genetically modified host cell is a genetically modified version of a parent cell that does not normally produce artemisinic epoxide or artemisinin. In some embodiments, the parent host cell is a eukaryotic host cell that does not normally produce artemisinic epoxide or artemisinin. In other embodiments, the parent cell is a prokaryotic host cell that does not normally produce artemisinic epoxide or artemisinin. In some embodiments, the parent cell is a prokaryotic host cell that does not normally synthesize isopentenyl pyrophosphate (IPP) via a mevalonate pathway.

Eukaryotic Host Cells

In some embodiments, where a subject genetically modified host cell is a eukaryotic host cell that does not normally synthesize artemisinic epoxide or artemisinin, the genetically modified host cell comprises one or more heterologous nucleic acids comprising nucleotide sequences encoding a subject variant P450 enzyme and one or more of: i) an ADS; ii) an FPP synthase; and iii) an IPP isomerase. In some embodiments, where the genetically modified host cell is a eukaryotic host cell that does not normally synthesize artemisinic epoxide or artemisinin, and where the eukaryotic host cell is one that does not normally synthesis IPP via a DXP pathway, the genetically modified host cell comprises one or more heterologous nucleic acids comprising nucleotide sequences encoding a subject variant P450 enzyme and one or more of: i) an ADS; ii) an FPP synthase; and iii) an IPP isomerase and iv) one or more DXP pathway enzymes. Nucleotide sequences encoding ADS, FPP synthase, IPP isomerase, and DXP pathway enzymes that are suitable for use in generating a subject genetically modified host cell are described above, as are expression vectors comprising the nucleotide sequences.

In some embodiments, the heterologous nucleic acids are present in one or more expression vectors. In some embodiments, the heterologous nucleic acids are present in two or more separate expression vectors. For example, in some embodiments, heterologous nucleic acids comprising nucleotide sequences encoding ADS are present in a first expression vector; and at least the heterologous nucleic acid comprising a nucleotide sequence encoding the enzyme that oxidizes amorpha-4,11-diene to artemisinic-11,12-epoxide is present on a second expression vector. In other embodiments, heterologous nucleic acids comprising nucleotide sequences encoding the enzyme that oxidizes amorpha-4,11-diene to artemisinic-11,12-epoxide are present in a first expression vector; and one or more of the heterologous nucleic acids comprising nucleotide sequences encoding FPP synthase and ADS are present on a second expression vector. As another example, in some embodiments, heterologous nucleic acids comprising nucleotide sequences encoding the enzyme that oxidizes amorpha-4,11-diene to artemisinic-11,12-epoxide and the ADS are present in a first expression vector; and one or more of the heterologous nucleic acids comprising nucleotide sequences encoding FPP synthase and IPP isomerase are present on a second expression vector.

Suitable eukaryotic host cells are described above. Suitable eukaryotic host cells include, but are not limited to, yeast cells, insect cells, plant cells, fungal cells, and algal cells. Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. In some embodiments, the host cell is a eukaryotic cell other than a plant cell.

In some embodiments, a subject genetically modified eukaryotic host cell comprises, addition to one or more heterologous nucleic acids encoding a variant P450 enzyme and one or more additional enzymes (e.g., an ADS, an FPP synthase, an IPP isomerase, one or more MEV pathway enzymes), as described above, one or more additional genetic modifications.

In some embodiments, a genetically modified eukaryotic host cell further comprises one or more genetic modifications that provide for one or more of: a) increased prenyltransferase activity levels; and b) decreased squalene synthase levels.

In some embodiments, a genetically modified eukaryotic host cell is further genetically modified such that the level of geranyl diphosphate synthase (GPPS) and/or farnesyl diphosphate synthase (FPPS) activity is increased. See, e.g., WO 2006/014837.

In some embodiments, a subject genetically modified eukaryotic host cell further comprises one or more genetic modifications that provide for decreased squalene synthase levels. The enzyme squalene synthase catalyzes a reaction that converts farnesyl diphosphate into squalene. This step is the first step in the pathway leading from farnesyl diphosphate to ergosterol. Thus by limiting the action of this enzyme, FPP is shunted towards terpenoid production pathways utilizing, e.g., terpene synthases or GGPP synthase and subsequent terpene synthases. See, e.g., WO 2006/014837.

In other embodiments, a subject genetically modified eukaryotic host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, a subject genetically modified eukaryotic host cell is one that is genetically modified to include one or more nucleic acids comprising a nucleotide sequence(s) that encode DXP biosynthetic pathway gene product(s); and nucleotide sequences encoding flavodoxin and a corresponding flavodoxin reductase.

Prokaryotic Host Cells

In some embodiments, where a subject genetically modified host cell is a prokaryotic cell that does not normally synthesize artemisinic epoxide or artemisinin, the genetically modified host cell comprises one or more heterologous nucleic acids comprising nucleotide sequences encoding a subject variant P450 enzyme and one or more of: i) an ADS; ii) an FPP synthase; and iii) an IPP isomerase. In some embodiments, where a subject genetically modified host cell is a prokaryotic cell that does not normally synthesize artemisinic epoxide or artemisinin, and where the prokaryotic cell does not normally synthesize IPP via a mevalonate pathway, the genetically modified host cell comprises one or more heterologous nucleic acids comprising nucleotide sequences encoding a subject variant P450 enzyme and one or more of: i) an ADS; ii) an FPP synthase; iii) an IPP isomerase; and iv) one or more mevalonate pathway enzymes.

In some embodiments, the heterologous nucleic acids are present in one or more expression vectors. In some embodiments, the heterologous nucleic acids are present in two or more separate expression vectors. For example, in some embodiments, heterologous nucleic acids comprising nucleotide sequences are present in a first expression vector, and at least the heterologous nucleic acid comprising a nucleotide sequence encoding the variant P450 enzyme is present on a second expression vector. For example, in some embodiments, a heterologous nucleic acid comprising a nucleotide sequence encoding the variant P450 enzyme is present in a first expression vector; and one or more heterologous nucleic acids comprising nucleotide sequences encoding FPP synthase and ADS are present on a second expression vector.

Multiple heterologous nucleotide sequences can be operably linked in a single operon within a vector, or can be provided as multiple operons in one or a plurality of vectors. For example, a single expression vector can comprise at least two, three, four, five, or all of the heterologous sequences encoding the entire mevalonate pathway enzymes, where the expression of each of the enzymes is present in one or more operons (e.g., two operons). Where desired, two expression vectors can be employed, each of which contains one or more heterologous sequences operably linked in a single operon.

In some embodiments, a subject genetically modified host cell comprises heterologous nucleic acids comprising nucleotide sequences encoding: a) a variant P450 enzyme; b) mevalonate pathway enzymes MK, PMK, and MPD; c) an FPP synthase; and d) an ADS. In these embodiments, the genetically modified host cell produces artemisinic epoxide when cultured in a suitable culture medium comprising mevalonate. In some embodiments, a subject genetically modified host cell comprises heterologous nucleic acids comprising nucleotide sequences encoding: a) a variant P450 enzyme; b) mevalonate pathway enzymes MK, PMK, and MPD; c) a heterologous IPP isomerase; d) an FPP synthase; and e) an ADS. In these embodiments, the genetically modified host cell produces artemisinic epoxide when cultured in a suitable culture medium comprising mevalonate.

In other embodiments, a subject genetically modified host cell comprises heterologous nucleic acids comprising nucleotide sequences encoding: a) a variant P450 enzyme; b) mevalonate pathway enzymes acetoacetyl-CoA thiolase, HMGS, HMGR, MK, PMK, and MPD; c) an FPP synthase; and d) an ADS. In these embodiments, the genetically modified host cell produces artemisinic epoxide when cultured in a suitable culture medium. In some embodiments, the acetoacetyl-CoA thiolase, the HMGS, and the HMGR are encoded in a first operon; and the MK, PMK, and MPD are encoded in a second operon. In other embodiments, a subject genetically modified host cell comprises heterologous nucleic acids comprising nucleotide sequences encoding: a) a variant P450 enzyme; b) mevalonate pathway enzymes acetoacetyl-CoA thiolase, HMGS, HMGR, MK, PMK, and MPD; c) a heterologous IPP isomerase; d) an FPP synthase; and e) an ADS. In these embodiments, the genetically modified host cell produces artemisinic epoxide when cultured in a suitable culture medium. In some embodiments, the acetoacetyl-CoA thiolase, the HMGS, and the HMGR are encoded in a first operon; and the MK, PMK, and MPD are encoded in a second operon.

Suitable host cells include any of a variety of non-pathogenic laboratory strains of prokaryotic host cells, as described above. Suitable prokaryotic cells include, but are not limited to, any of a variety of non-pathogenic laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Non-limiting examples of suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. In some embodiments, the host cell is *Escherichia coli*. Examples of *Escherichia coli* strains that can be employed include, but are not limited to, common cloning strains such as DH1, B, MG1655, W3110, BL21, DH10B, JM109, DH5alpha, XL1-Blue, XL2-Blue, MC1000, KY3276, W1485, HB101, No. 49, NY49, MP347, NM522, and derivatives thereof. Other suitable prokaryotic host cells are described above. In some embodiments, the host cell is one that does not normally produce IPP via a mevalonate pathway.

In some embodiments, a subject genetically modified prokaryotic host cell has a functional endogenous DXP pathway. In other embodiments, a subject genetically modified prokaryotic host cell has a functionally disabled endogenous DXP pathway. In other embodiments, a subject genetically modified prokaryotic host cell has a functionally disabled endogenous tryptophanase A gene.

Generating a Genetically Modified Host Cell

To generate a subject genetically modified host cell, the one or more heterologous nucleic acids is introduced stably or transiently into a parent host cell, using established techniques, including, but not limited to, electroporation, calcium phosphate precipitation, DEAE-dextran mediated transfection, liposome-mediated transfection, and the like.

Producing Artemisinic Epoxide and Downstream Products

Production of artemisinic epoxide is carried out by culturing a subject genetically modified host cell in a suitable medium under conditions that provide for production of the enzymes encoded by the heterologous nucleic acid(s), and production of artemisinic epoxide. The artemisinic epoxide so produced can be isolated from a lysate of the cells, from the cell culture medium, or both.

In some embodiments, a subject genetically modified host cell is cultured in a suitable medium (e.g., Luria-Bertoni broth, optionally supplemented with one or more additional agents, such as an inducer (e.g., where one or more of the heterologous nucleotide sequences is under the control of an inducible promoter), etc.); and the culture medium is overlaid with an organic solvent, e.g. dodecane, forming an organic layer. The artemisinic epoxide produced by the genetically modified host cell can be purified from one or more of the culture medium, a cell, a cell lysate, and a fractionated cell lysate. In some embodiments, where a heterologous nucleotide sequence is operably linked to an inducible promoter, an inducer is added to the culture medium; and, after a suitable time, the artemisinic epoxide is isolated from one or more of the culture medium, a cell, a cell lysate, and a fractionated cell lysate. In some embodiments, the artemisinic epoxide is separated from other products which may be present in one or more of the culture medium, a cell, a cell lysate, and a fractionated cell lysate. Separation of the artemisinic epoxide from other products that may be present is readily achieved using, e.g., standard chromatographic techniques.

The artemisinic epoxide can be isolated from the cell culture medium and/or a cell lysate using standard purification methods well known in the art, including, e.g., high performance liquid chromatography, gas chromatography, and other standard chromatographic methods.

In some embodiments, the artemisinic epoxide synthesized by a genetically modified host cell is further chemically modified in a cell-free reaction. Thus, the present invention provides methods of producing artemisinin and/or an intermediate between artemisinic epoxide and artemisinin. For example, in some embodiments, artemisinic epoxide is produced by a genetically modified host cell, as described above; the artemisinic epoxide is isolated from culture medium and/or a cell lysate; and the artemisinic epoxide is further chemically modified in a cell-free reaction to generate artemisinin and/or an intermediate between artemisinic epoxide and artemisinin. Thus, e.g., in some embodiments, the artemisinic epoxide is recovered from the cell culture medium in which the genetically modified host cells are cultured and/or is recovered from the genetically modified host cells; and the recovered artemisinic epoxide is further modified chemically (e.g., in a cell-free reaction) to generate one or more downstream product(s) such as artemisinic-11,12-diol, artemisinic alcohol, artemisinic aldehyde, artemisinic acid, and artemisinin. Artemisinic-11,12-epoxide is reacted with a strong base to yield artemisinic-11,12-diol, which spontaneously dehydrates to form artemisinic alcohol. Methods of converting artemisinic acid to artemisinin are known in the art, and any such method can be used. See, e.g., Acton and Roth (1992) *J. Org. Chem.* 57:3610-3614; and U.S. Patent Publication No. 2006/0270863.

In some embodiments, the artemisinic epoxide is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of artemisinic epoxide refers to artemisinic epoxide that is free from side products, macromolecules, contaminants, etc.

In some embodiments, the artemisinin produced, and/or the intermediate between artemisinic epoxide and artemisinin (e.g., the artemisinic alcohol, artemisinic aldehyde, artemisinic acid, etc.) art, is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of artemisinin or the intermediate refers to artemisinic epoxide that is free from side products, macromolecules, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation of Expression Constructs

Construction of pAM36-MevT66, pMevB-Cm, pMBI, pMBIS, pAM45, and pAM92 is described.

pAM36-MevT66

Expression plasmid pAM36-MevT66 was generated by inserting the MevT66 operon into the pAM36 vector. The pAM36 vector was generated by inserting an oligonucleotide cassette containing AscI-SfiI-AsiSI-XhoI-PacI-FsII-PmeI restriction sites into the pACYC184 vector (GenBank accession number X06403), and by removing the tetracycline resistance conferring gene in pACYC184. The MevT66 operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The operon was synthetically generated and comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 . . . 3285), all three sequences being codon-optimized for expression in *Escherichia coli*. The synthetically generated MevT66 operon was flanked by a 5' EcoRI restriction site and a 3' Hind III restriction site, and could thus be cloned into compatible restriction sites of a cloning vector such as a standard pUC or pACYC origin vector. From this construct, the MevT66 operon was PCR amplified with flanking SfiI and AsiSI restriction sites, the amplified DNA fragment was digested to completion using SfiI and AsiSI restriction enzymes, the reaction mixture was resolved by gel electrophoresis, the approximately 4.2 kb DNA fragment was gel extracted using a gel purification kit (Qiagen, Valencia, Calif.), and the isolated DNA fragment was ligated into the SfiI AsiSI restriction site of the pAM36 vector, yielding expression plasmid pAM36-MevT66.

pMevB-Cm

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 . . . 1911) (encodes a mevalonate kinase), the ERG8 gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate carboxylase), and by splicing the PCR fragments together using overlap extensions (SOE-ing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the approximately 4.2 kb DNA fragment, and ligating the isolated DNA fragment into the PstI restriction site of vector pBBR1MCS-1 (Kovach et al., *Gene* 166(1): 175-176 (1995)), yielding expression plasmid pMevB-Cm.

pMBI

Expression plasmid pMBI was generated by inserting the MBI operon into the pBBR1MCS-3 vector. In addition to the enzymes of the MevB operon, the MBI operon also encodes an isopentenyl pyrophosphate isomerase, which catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends, digesting the amplified DNA fragment to completion using XmaI restriction enzyme, resolving the reaction mixture by gel electrophoresis, gel extracting the approximately 0.5 kb fragment, and ligating the isolated DNA fragment into the XmaI restriction site of expression plasmid pMevB-Cm, thereby placing idi at the 3' end of the MevB operon. The MBI operon was subcloned into the SalI SacI restriction site of vector pBBR1MCS-3 (Kovach et al., *Gene* 166(1): 175-176 (1995)), yielding expression plasmid pMBI (see U.S. Pat. No. 7,192,751).

pMBIS

Expression plasmid pMBIS was generated by inserting the ispA gene into pMBI. The ispA gene encodes a farnesyl pyrophosphate synthase, which catalyzes the condensation of two molecules of IPP with one molecule of DMAPP to make farnesyl pyrophosphate (FPP). The coding sequence of the ispA gene (GenBank accession number D00694, REGION: 484 . . . 1383) was PCR amplified from *Escherichia coli* genomic DNA using a forward primer with a SacII restriction site and a reverse primer with a SacI restriction site. The amplified PCR product was digested to completion using SacII and SacI restriction enzymes, the reaction mixture was resolved by gel electrophoresis, and the approximately 0.9 kb DNA fragment was gel extracted, and the isolated DNA fragment was ligated into the SacII SacI restriction site of pMBI, thereby placing the ispA gene 3' of idi and the MevB operon, and yielding expression plasmid pMBIS (see U.S. Pat. No. 7,192,751; and SEQ ID NO:4 of U.S. Pat. No. 7,183,089).

pAM45

Expression plasmid pAM45 was generated by inserting the MBIS operon into pAM36-MevT66 and adding lacUV5 promoters in front of the MBIS and MevT66 operons. The MBIS operon was PCR amplified from pMBIS using primers comprising a 5' XhoI restriction site and a 3' PacI restriction site, the amplified PCR product was digested to completion using XhoI and PacI restriction enzymes, the reaction mixture was resolved by gel electrophoresis, the approximately 5.4 kb DNA fragment was gel extracted, and the isolated DNA fragment was ligated into the XhoI PacI restriction site of pAM36-MevT66, yielding expression plasmid pAM43. A DNA fragment comprising a nucleotide sequence encoding the lacUV5 promoter was synthesized from oligonucleotides, and sub-cloned into the AscI SfiI and AsiSI XhoI restriction sites of pAM43, yielding expression plasmid pAM45.

pAM92

Figure 4:
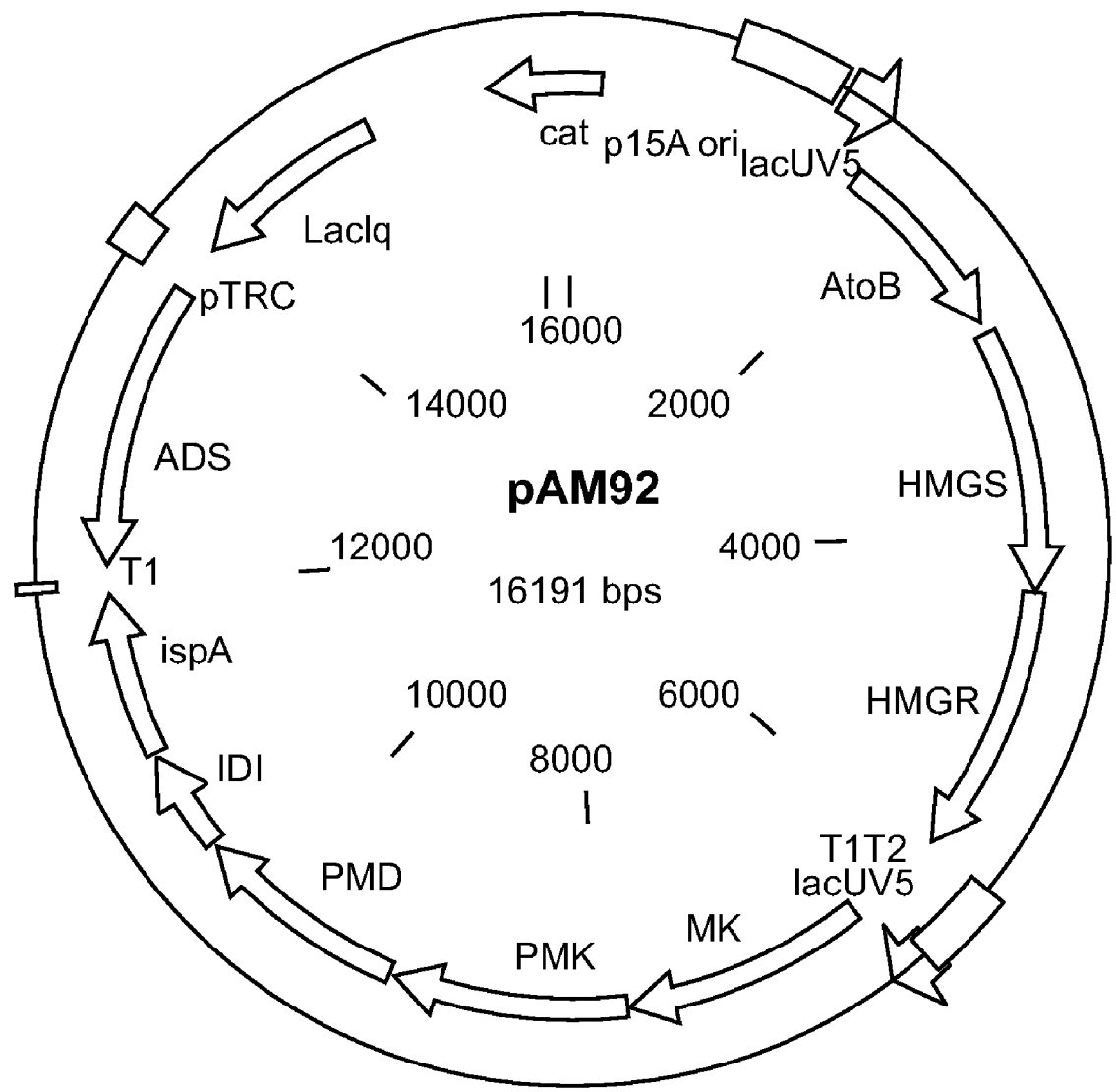
FIG. 4 is a schematic depiction of expression plasmid pAM92.

Expression plasmid pAM92 was generated by inserting a nucleotide sequence encoding an amorpha-4,11-diene synthase ("ADS") into pAM45. The nucleotide sequence encoding ADS was designed such that upon translation the amino acid sequence of the enzyme would be identical to that described by Merke et al. (2000) *Ach. Biochem. Biophys.* 381:173-180. The nucleotide sequence encoding ADS was codon-optimized for expression in *Escherichia coli* (see U.S. Pat. No. 7,192,751). The nucleotide sequence of pAM92 is given as SEQ ID NO:9. A plasmid map of pAM92 is shown in FIG. 4.

Example 2

Constructs Encoding Cytochrome P450$_{BM3}$ (CYP102) or Variants Thereof

Expression plasmid pTrcBM3 was generated by inserting into vector pTrc99A a nucleotide sequence encoding the cytochrome P450$_{BM3}$ of *Bacillus megaterium*, codon-optimized for expression in *Escherichia coli* (SEQ ID NO:5). A DNA fragment comprising this codon-optimized nucleotide sequence was generated synthetically, and inserted into the NcoI HindIII site of vector pTrc99A, yielding expression plasmid pTrcBM3.

Expression plasmids pTrcBM3-14-G1 and pTrcBM3-14-G3 were generated by substituting nucleotide sequences within pTrcBM3 that encode specific domains of cytochrome P450$_{BM3}$. Specifically, the G1 variant comprises nucleotide substitutions that translate into a substitution at amino acid 87 from phenylalanine to alanine; and the G3 variant comprises nucleotide substitutions that translate into a substitution at amino acid 87 from phenylalanine to alanine, at amino acid 47 from arginine to leucine, and at amino acid 51 from tyrosine to phenylalanine. The expression plasmids were generated by rational design using overlap PCR. Two DNA fragments were created. One DNA fragment encoded the N-terminus of the cytochrome P450$_{BM3}$ domain to the C-terminus of the desired mutation, and was generated using primer BM3:NcoI-F (SEQ ID NO:12) and primer F87A-R or R57L/Y51F-R (SEQ ID NOs:13 or 14, respectively). A second DNA fragment encoded the N-terminus of the desired mutation to the C-terminus of the cytochrome P450$_{BM3}$ domain, and was generated using primer BM3:SacI-R (SEQ ID NO:15) and primer F87A-F or R47L/Y51F-F (SEQ ID NOs:

16 or 17, respectively). Both DNA fragments were amplified by PCR: 98° C. for 30 seconds, 50° C. for 45 seconds, 72° C. for 60 seconds, repeated 30 times. The reaction mixture contained 1× Phusion buffer, 0.2 mM dNTP, 0.5 µM forward and reverse primers, 2.5 U Phusion DNA polymerase, and 50 ng pTrcBM3 as a template in a final volume of 100 µL. The amplified DNA was gel extracted, and the two amplified DNA fragments were spliced together via overlap PCR using primers BM3:NcoI-F and BM3:SacI-R and the same PCR conditions as described above. The amplified DNA fragment was digested to completion using NcoI and SacI restriction enzymes, and cloned into the NcoI and SacI site of expression plasmid pTrcBM3, yielding expression plasmids pTrcBM3-G1 or pTrcBM3-G3.

Reduced expression of $P450_{BM3}$ variants improved artemisinic epoxide production, and so an additional six base pairs were introduced between the ribosome binding site (RBS) and the start codon at the NcoI restriction site of pTrcBM3. The RBS region was amplified by PCR: 98° C. for 30 seconds, 55° C. for 30 seconds, and 72° C. for 30° C. seconds, repeated 30 times. The reaction mixture contained 1× Phusion buffer, 0.2 mM dNTP, 0.5 µM forward and reverse primers (pTrc99a:RBS_6-F and pTrc99a:RBS_6-R; SEQ ID NOs: 5 and 6, respectively), 2.5 U Phusion DNA polymerase, and 50 ng pTrcBM3 as a template in a total volume of 100 µL. The amplified DNA fragment was digested using EcoRV and NcoI restriction enzymes, and was inserted into the EcoRV NcoI restriction site of pTrcBM3, yielding expression plasmid pTrcBM3-14.

Expression plasmids pTrcBM3-14-G1 and pTrcBM3-14-G3 were generated by transferring the BM3 variant sequences of pTrcBM3-G1 or pTrcBM3-G3, respectively, into expression vector pTrcBM3-3-14. Expression vectors pTrcBM3-G1 or pTrcBM3-G3 were digested to completion using restriction enzymes NcoI and HindIII, the reaction mixture was resolved by gel electrophoresis, the DNA fragment comprising the BM3 variant sequence was gel purified, and the isolated DNA fragment was inserted into the NcoI and HindIII restriction site of expression plasmid pTrcBM3-14, yielding expression plasmid pTrcBM3-14-G1 or pTrcBM3-14-G3.

Expression plasmids pTrcBM3-14-G4 (G3+A328L) and further pTrcBM3-14 variants comprising substitutions at amino acid positions F87, I263, A264, and A328 were generated by site-directed saturation mutagenesis of cytochrome $P450_{BM3}$. For each amino acid position, two DNA fragments were created. One DNA fragment encoded the N-terminus of the cytochrome $P450_{BM3}$ domain to the C-terminus of the desired mutation, and was generated using primer BM3:NcoI-F (SEQ ID NO:12) and primer 87R, 263R, 264R, or 328R (SEQ ID NOs:18, 19, 20, or 21, respectively). A second DNA fragment encoded the N-terminus of the desired mutation to the C-terminus of the cytochrome $P450_{BM3}$ domain, and was generated using primer BM3:SacI-R (SEQ ID NO:15) and primer 87F, 263F, 264F, or 328F (SEQ ID NOs: 22, 23, 24, or 25, respectively). Both DNA fragments were amplified by PCR: 98° C. for 30 seconds, 50° C. for 45 seconds, 72° C. for 60 seconds, repeated 30 times. The reaction mixture contained 1× Phusion buffer, 0.2 mM dNTP, 0.5 µM forward and reverse primers, 2.5 U Phusion DNA polymerase, and 50 ng pTrcBM3 as a template in a final volume of 100 µL. The amplified DNA was gel extracted, and the two amplified DNA fragments were spliced together via overlap PCR using primers BM3:NcoI-F and BM3:SacI-R and the same PCR conditions as described above. The amplified DNA fragment was digested to completion using NcoI and SacI restriction enzymes, and cloned into the NcoI and SacI site of expression plasmid pTrcBM3-14. For each amino acid position undergoing saturation mutagenesis, 120 colonies from the resulting transformation were screened by DNA sequencing to obtain all 20 possible amino acid substitutions.

Example 3

Production of Artemisinic Epoxide from amorpha-4,11-diene Produced Via the MEV Pathway in *Escherichia coli* Host Strains Host strains were created by transforming chemically competent *Escherichia coli* DH1 cells with pAM92 and pTrcBM3-14, pTrcBM3-14-G1, pTrcBM3-14-G3, pTrcBM3-G4(A328L), or pTrcBM3-G4(A328N).

Pre-cultured host cell transformants were inoculated into fresh Terrific Broth (TB) supplemented with 2% glycerol (v/v), 65 mg l$^{-1}$ δ-aminolevulinic acid hydrochloride (ALA), and 50 µg/mL each of carbenicillin and chloramphenicol. All cultures were inoculated at an optical density at a wavelength of 600 nm ($OD_{600}$) of 0.05. Cultures were induced with 0.05 mM IPTG upon reaching an $OD_{600}$ of 0.25. After 24 or 48 hours of culture at 30° C., 100 µL of culture was extracted with 900 µL ethyl acetate spiked with caryophellene (5 µg/mL) as an internal standard.

The organic layer was sampled and analyzed by gas chromatography-mass spectrometry (GC-MS) using a Polaris Q gas chromatograph (70 eV, Thermo Electron Corp., Waltham, Mass.) equipped with a DB5 capillary column (30 m×0.25 mm internal diameter, 0.25 µm film thickness; Agilent Technologies, Palo Alto, Calif.) and a TriPlus auto sample-injector (Thermo Electron Corp., Waltham, Mass.). The gas chromatography program used was 100° C. for 5 minutes, then ramping 30° C./min to 150° C., 5° C./min to 180° C., and 50° C./min to 300° C. Quantification of artemisinic epoxide production was carried out by generating a calibration curve using the GC peak areas from artemisinic epoxide standards of known concentration. To confirm analysis of chemical structures, $^1$H-nuclear magnetic resonance ($^1$H-NMR) spectroscopy was performed in $CDCl_3$ (Cambridge Isotope Laboratories; Cambridge, Mass.) at 25° C. on a Bruker AV-500 or AV-400 spectrometer at the University of California, Berkeley, College of Chemistry NMR Facility.

Figure 5A:
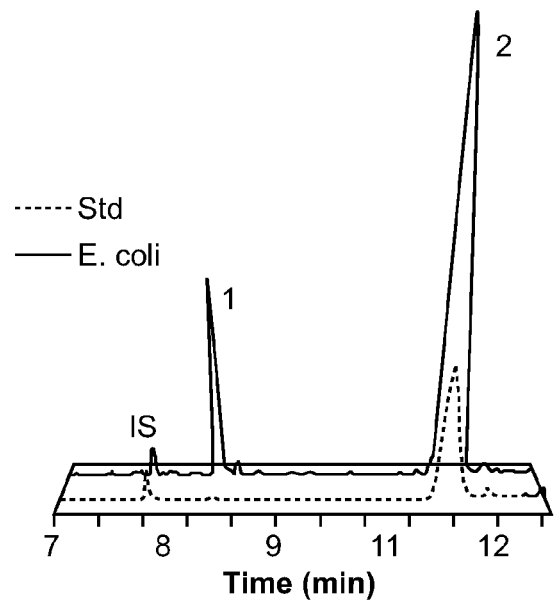
FIG. 5A depicts full scan GC-MS traces of artemisinic-11S,12-epoxide that was synthesized chemically (2), and amorpha-4,11-diene (1) and artemisinic-11S,12-epoxide (2) that was produced by an *Escherichia coli* DH1 host strain harboring expression plasmids pAM92 and pTrcBM3-14-G4.
Figure 5B:
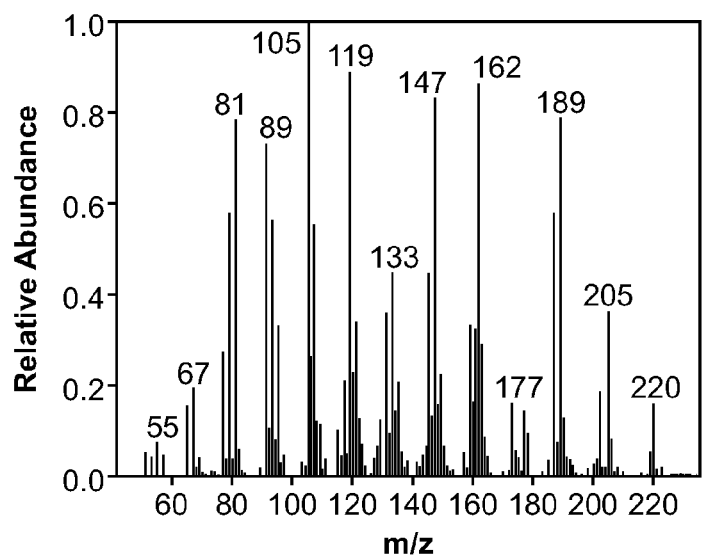
FIGS. 5B-C depict the mass spectra of artemisinic-11S,12-epoxide synthesized chemically (B) or produced by an *Escherichia coli* DH1 host strain (C).
Figure 5C:
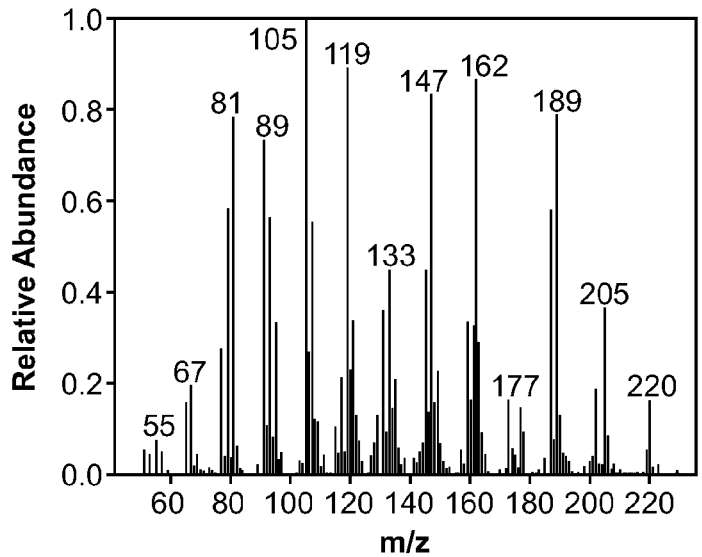
Figure 6A:
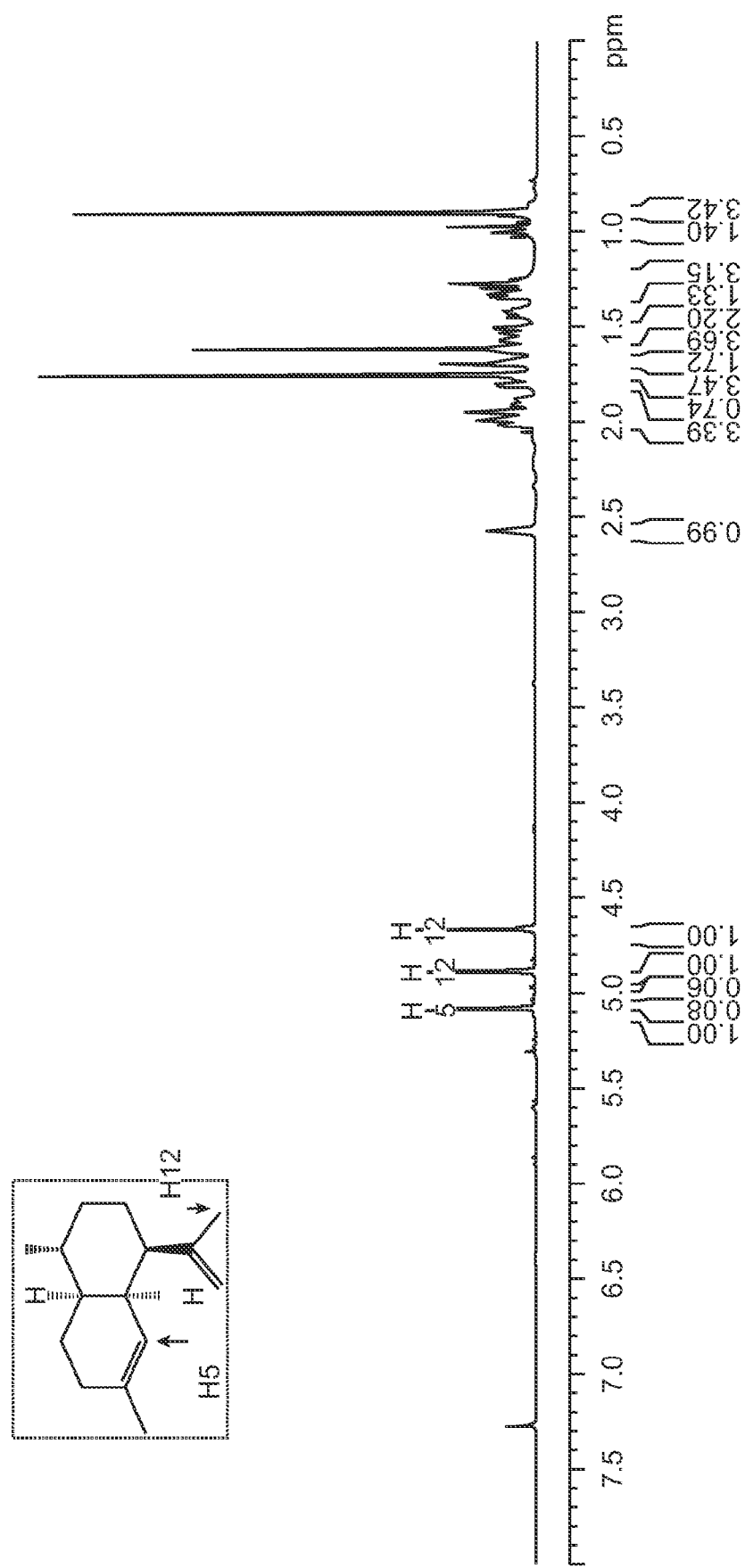
FIGS. 6A-C depict $^1$H-NMR spectra (500 Mhz) of an amorphadiene standard (A), chemically synthesized artemisinic-11S,12-epoxide (B), and artemisinic-11S,12-epoxide produced by an *Escherichia coli* DH1 host strain (C).
Figure 6B:
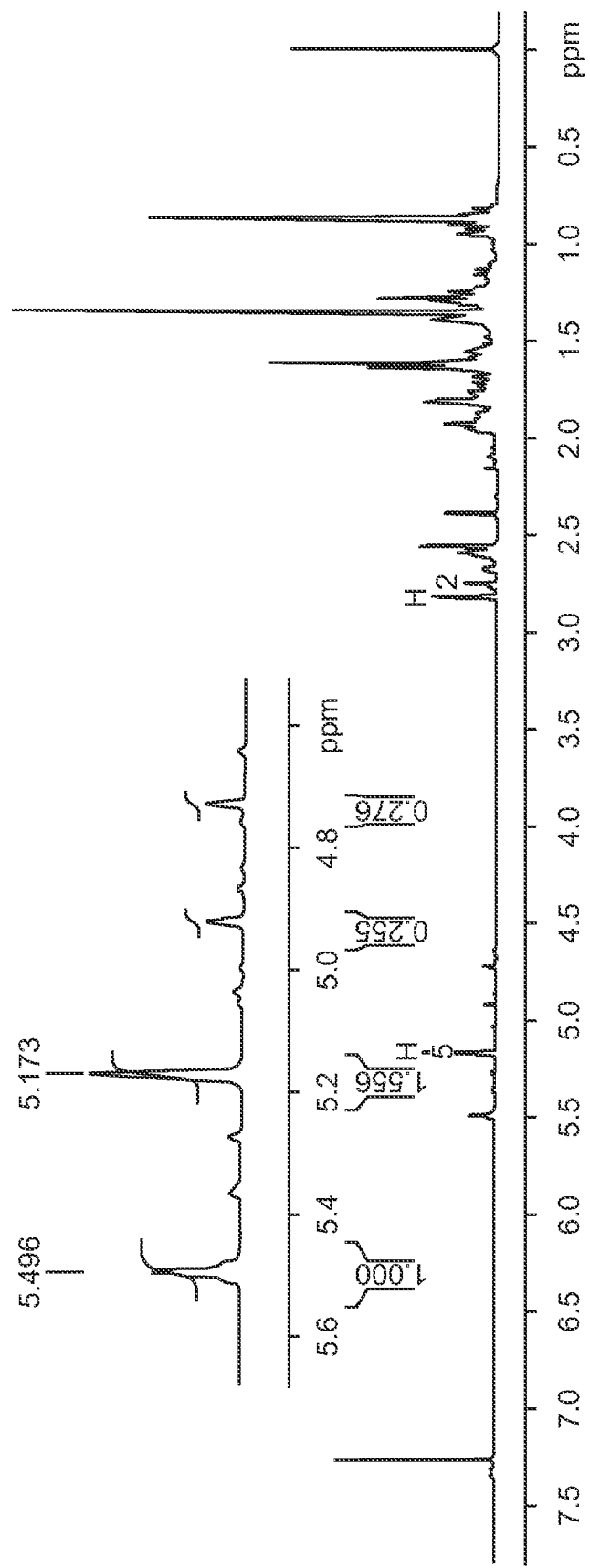
Figure 6C:
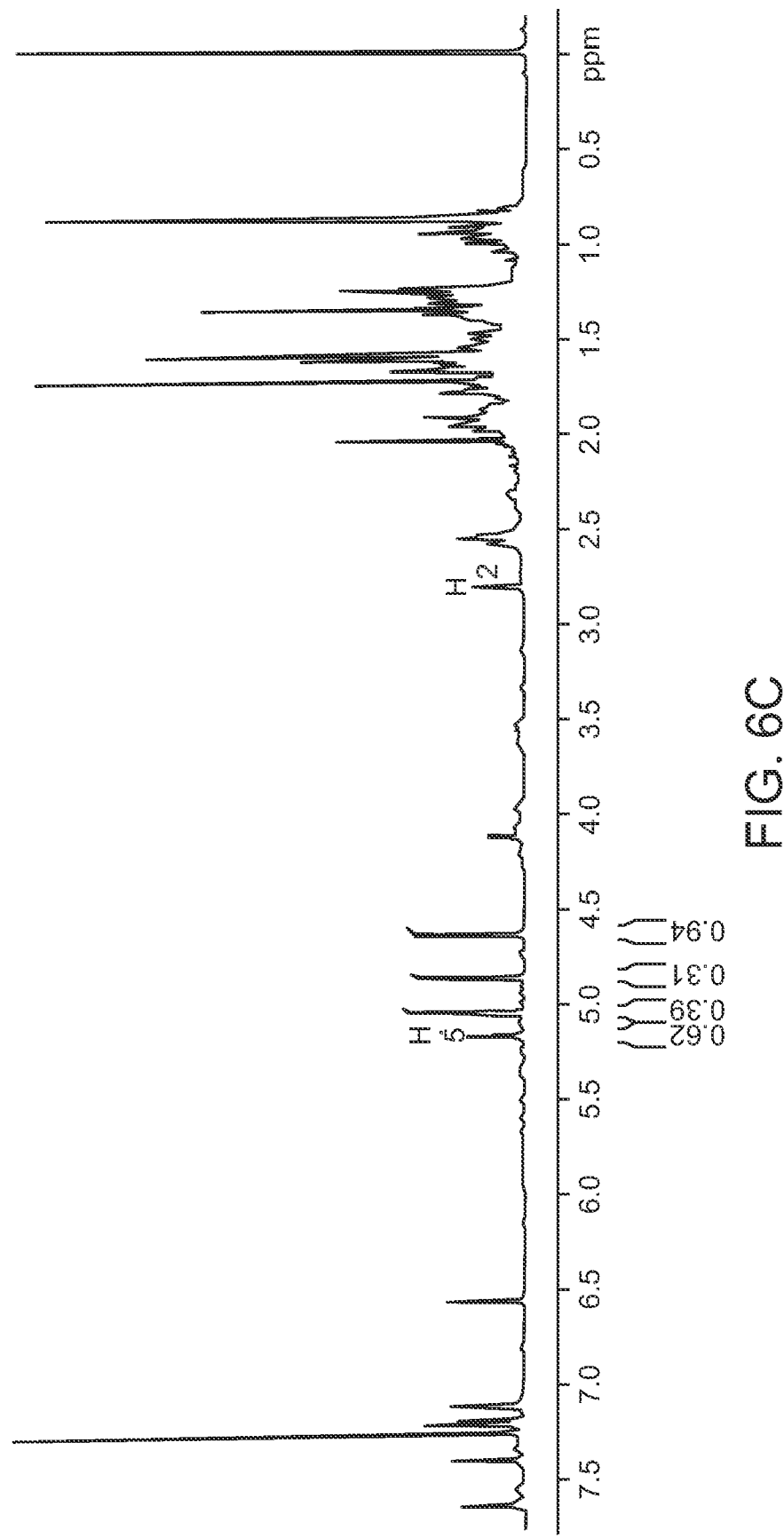

Host cells harboring pAM92 and pTrcBM3-14-G1 or pTrcBM3-14-G3 produced a single compound that had identical retention times and electron-impact mass spectra to chemically synthesized artemisinic-11S,12-epoxide (FIG. 5). $^1$H-nuclear magnetic resonance ($^1$H-NMR) spectroscopy confirmed analysis of the chemical structure (FIG. 6). A host strain harboring pAM92 and pTrcBM3-14-G1 yielded 140±50 mg/L artemisinic epoxide (mean ±S.D. of triplicate measurements), a host strain harboring pAM92 and pTrcBM3-14-G3 yielded 200±50 mg/L, a host strain harboring pAM92 and pTrcBM3-14-G4(A328L) yielded greater than 550 mg/L artemisinic epoxide, and a host strain harboring pAM992 and pTrcBM3-14-G4(A328N) yielded a 3-fold increase in artemisinic epoxide production over host strains harboring pAM92 and pTrcBM3-14-G3.

Saturation mutagenesis at any of the four positions (F87, I263, A264, and A328) did not substantially alter the distribution of oxidized amorphadiene metabolites. In nearly all cases, artemisinic-11S,12-epoxide remained the sole product. Variant G3+I263G produced both artemisinic epoxide epimers, with a 20% epimeric enrichment for the S form. Additionally, variant G3+F87G yielded several oxidized amorphadiene metabolites. Variant G3+F87G yielded both the R and S artemisinic epoxide epimers (50% enrichment for S) as well as three additional peaks, which likely correspond to ketones in which hydroxylation occurred on the aromatic rings.

Example 4

Generation of *Escherichia coli* Host Strains Harboring a Functionally Disabled Tryptophanase A (tnaA) Gene The tnaA gene, which encodes a native tryptophanase A enzyme, was knocked out in *Escherichia coli* strain DH1 according to an established method (Datsenko and Wanner (2000) *Proc. Natl. Acad. Sci. USA* 97:6640-6645). Amorpha-4,11-diene, artemisinic epoxide, and indigo production of this strain was compared to that of its parent strain. Cultures were grown and sampled as described in Example 3.

The tnaA knockout strain provided increased yields of amorpha-4,11-diene (1.36-fold increase) and artemisinic epoxide (1.72-fold increase), but produced no measurable quantities of indigo. The yield of artemisinic epoxide for the tnaA knockout strain was 1210±170 mg/L (n=9).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified host cell, wherein the genetically modified host cell produces amorpha-4,11-diene, wherein the genetically modified host cell comprises a heterologous cytochrome P450 enzyme that converts the produced amorpha-4,11-diene into amorpha-4-ene-11,12-epoxide, and wherein the genetically modified host cell is a yeast cell or a bacterial cell.

2. The genetically modified host cell of claim 1, wherein the amorpha-4,11-diene is produced via a 1-deoxy-D-xylulose 5-diphosphate (DXP) pathway.

3. The genetically modified host cell of claim 1, wherein the host cell comprises a heterologous nucleotide sequence encoding one or more enzymes of the DXP pathway.

4. The genetically modified host cell of claim 1, wherein the amorpha-4,11-diene is produced via a mevalonate pathway.

5. The genetically modified host cell of claim 1, wherein the host cell comprises a heterologous nucleotide sequence encoding one or more enzymes of the mevalonate pathway.

6. The genetically modified host cell of claim 1, wherein the host cell is a yeast cell.

7. The genetically modified host cell of claim 6, wherein the yeast cell is *Saccharomyces cerevisiae*.

8. The genetically modified host cell of claim 1, wherein the host cell is a bacterial cell.

9. The genetically modified host cell of claim 8, wherein the host cell is *Escherichia coli*.

* * * * *